United States Patent [19]
Little, II

[11] Patent Number: 5,807,818
[45] Date of Patent: Sep. 15, 1998

[54] THERAPEUTIC USES OF BACTERICIDAL/PERMEABILITY INCREASING PROTEIN (BPI) PROTEIN PRODUCTS

[75] Inventor: Roger G. Little, II, Benicia, Calif.

[73] Assignee: Xoma Corporation, Berkeley, Calif.

[21] Appl. No.: 435,855

[22] Filed: May 5, 1995

Related U.S. Application Data

[62] Division of Ser. No. 415,158, Mar. 31, 1995, Pat. No. 5,639,727, which is a continuation of Ser. No. 93,202, Jul. 15, 1993, abandoned, which is a continuation-in-part of Ser. No. 30,644, Mar. 12, 1993, Pat. No. 5,348,942.

[51] Int. Cl.$^6$ .......................... A61K 38/02; A61K 38/16
[52] U.S. Cl. .................................................. 514/2; 514/12
[58] Field of Search .............................................. 514/2, 12

[56] References Cited

U.S. PATENT DOCUMENTS

| | | | |
|---|---|---|---|
| 5,086,164 | 2/1992 | Maione et al. | 530/324 |
| 5,112,946 | 5/1992 | Maione | 530/324 |
| 5,171,739 | 12/1992 | Scott et al. | 514/12 |
| 5,221,664 | 6/1993 | Berkowitz et al. | 514/6 |
| 5,420,019 | 5/1995 | Theofan et al. | 435/69.1 |
| 5,639,727 | 6/1997 | Little, II | 514/12 |
| 5,652,332 | 7/1997 | Little, II | 530/324 |

FOREIGN PATENT DOCUMENTS

| | | |
|---|---|---|
| WO 90/09183 | 8/1990 | WIPO . |
| WO 92/01003 | 1/1992 | WIPO . |
| WO 92/02240 | 2/1992 | WIPO . |
| WO 92/03535 | 3/1992 | WIPO . |
| WO 92/09621 | 6/1992 | WIPO . |
| WO 93/13794 | 7/1993 | WIPO . |

OTHER PUBLICATIONS

Ginsburg et al. Killing of endothelial cells and release of arachodonic acid. Synergistic effects among hydrogen peroxide, membrane–damaging agents, cationic substances, and proteinases and their modulation by inhibitors. Inflammation. vol. 17, No. 3, pp. 295–319, Jun. 1993.

Nygaard et al. Defensins reduce the barrier integrity of a cultured epithelial monolayer without cytotoxicity. American Journal of Respiratory Cell and Molecular Biology. vol. 8, No. 2, pp. 193–200, Feb. 1993.

Okrent et al. Direct cytotoxicity of polymorphonuclear leukocyte granule proteins to human lung–derived cells and endothelial cells. American Review of Respiratory Disease. vol. 141, No. 1, pp. 179–185, Jan. 1990.

Azizkahan et al., "Mast Cell Heparin Stimulates Migration of Capilary Endothelial Cells in Vitro", *J. Exp. Med.,* 152:931–944 (Oct. 1980).

Castellot et al., "Heparin Protentiation of 3T3–Adipocyte Stimulated Angiogenesis: Mechanism of Action on Endothelial Cells", *J. Cell. Phys.,* 127:328–329 (1986).

Charles et al., "The Three–Dimensional Structure of Bovine Platelet Factor 4 at 3.0 A Resolution", *J. Biol. Chem.,* 264(4):2092–2099 (Feb. 5, 1989).

Cook et al., "Platelet Factor 4 Efficiently Reverses Heparin Anticoagulation in the Rat Without Adverse Effects of Heparin–Protamine Complexes", *Circulation,* 85(3):1102–1109 (Mar. 1992).

(List continued on next page.)

Primary Examiner—Elizabeth C. Kemmerer
Assistant Examiner—Brian Lathrop
Attorney, Agent, or Firm—McAndrews, Held & Malloy, Ltd.

[57] ABSTRACT

The present invention provides therapeutic methods for treatment of conditions including the neutralization of the anti-coagulant activity of heparin, inhibition of angiogenesis, tumor and endothelial cell proliferation, and treatment of chronic inflammatory diseases by administration of bactericidal/permeability-increasing (BPI) protein products.

2 Claims, 31 Drawing Sheets

OTHER PUBLICATIONS

Folkman et al., "Abiogenesis and Inflammation", *Inflammation: Basic Principles and Correlates,* 2nd Ed., Review Press, Ltd., Chapter 40, pp. 821–839 (1992).

Gallagher, "Heparan Sulphates as Membrane Receptors for the Fibroblast Growth Factors", *Eur. J. Clin. Chem. Clin. Biochem.,* 32(4):239–247 (1994).

Gammon et al., "T Cell Determinant Structure: Cores and Determinant Envelopes in Three Major Mouse Histocompatibility Complex Halotypes", *J. Exp. Med.,* 173:609–617 (Mar. 1991).

Garcia et al., "Repligen IND for Platelet Factor", *Bio World Today,* p. 5 (Jan. 11, 1983).

Gazzano–Santoro et al., "High Affinity Binding of the Bactericidal/Permeability Increasing Protein and a Recombinant Amino–Terminal Fragment to the Lipid A Region of Lipopolysaccharide",*Infect. Immunol.,* 60(11):4754–4761 (Nov. 1992).

Gray et al., "Cloning of the cDNA of a Human Neutrophil Bactericidal Protein", *J. Biol. Chem.,* 264(16):9505–9509 (Jun. 5, 1989).

Heyderman et al., "Reduction of the Anticoagulant Activity of Glycosaminoglycans on the Surface of the Vascular Endothelium by Endotoxin and Neutrophils: Evaluation by an Amidolytic Assay", *Thrombosis Res.,* 67:677–685 (Apr. 28, 1992).

Hiti–Harper et al., "Platelet Factor 4: An Inhibitor of Collagenase", *Science,* 199:991–992 (Mar. 3, 1978).

Kaklamanis, "Expiermental Animal ModelsResembling Rheumatoid Arthritis", *Clin. Rheumatol.,* 11(1):41–47 (1992).

Little, "Functional Domains of Recombinant Bactericidal/Permeability Increasing Protein (rBPI$_{23}$)", *J. Biol. Chem.,* 269(3):1865–1872 (Jan. 1994).

Maeji et al., "Multi–Pin Peptide Strategy for T Cell Determinant Analysis", *J. Immunol. Methods,* 134:23–33 (1990).

Maione et al., "Inhibition of Tumor Growth in Mice by an Analogue of Platelet Factor 4 That Lacks Affinity for Heparin and Retains Potent Angiostatic Activity", *Cancer Res.,* 51:2077–2083 (Apr. 15, 1991).

Maione et al., *CAS BioTech Updates–Antibody Conjugates,* p. 1, 1334, 117:2260303x (Jun. 16, 1992).

Mannion et al., *J. Clin. Invest.,* 85:853–860 (Mar. 1990).

Marra et al., "The Role of Bactericidal/Permeability–Increasing Protein as a Natural Inhibitor of Bacterial Endotoxin", *J. Immunol.,* 148:532–537 (Jan. 15, 1992).

Marra et al., Aug. 23, 1990 (Abstract: WPI Accession No.: 90–274947/36).

Merrifield et al., "Instrument for Automated Synthesis of Peptides",*Anal. Chem.,* 38(13):1905–1914 (Dec. 1966).

Merrifield et al., "Solid Phase Peptide Synthesis", *J. Am. Chem. Soc.,* 85:2149–2154 (Jul. 20, 1963).

Miles et al., "Recombinant Platelet Factor 4 (rPF4) and a Non–Heparin Binding Derivative Inhibit AIDS–Kaposi Sarcoma Derived Cell Lines", *VII International Conference on AIDS Held in Florence Italy,* Paper 41(8), W.A. 1066 p. 108 (Jun. 16–21, 1991).

Mitchell et al., "Inhibitors of Angiogenesis", Chapter 16, in *Annual Reports in Medical Chemistry,* vol. 27, Academic Press, Inc. (1992).

Murav'Ev, *Ter. Ark.,* 52(11):126–129 (1980).

Ooi et al., "Endotoxin–Neutralizing Properties of the 25kD N–Terminal Fragment and a Newly Isolated 30 kD C–Terminal Fragment of the 55–60 kD Bactericidal/Permeability–Increasing Protein of Human Neutrophils", *J. Exp. Med.,* 174:649 (1991).

Passaniti et al., *Lab. Invest.,* 67:519–528 (1992).

Peacock et al., "Angiobiogenesis Inhibition Suppresses Collagen Arthritis", *J. Exp. Med.,* 175:1135–1138 (Apr. 1992).

Redini et al., *Biochem. J.,* 252(2):515–519 (1980).

Repligen Corporation, *Research in Review,* (Spring 1992).

Stuart et al., "Nature and the Specificity of the Immune Response to Collagen–Induced Arthritis in Mice." *J. Clin. Invest.,* 69:673–683 (Mar. 1982).

Takayama et al., "Absence of Lipopolysaccharide in the Lyme Disease Spirochete." *Infect. and Immunol.,* 55(9):2311–2312 (Sep. 1987).

St. Charles et al., *The Journal of Biological Chemistry,* 264(4):2092–2099 (1989).

Taylor et al., "Protamine in an Inhibitor of Angiogenesis." *Nature,* 297:307–312 (May 27, 1982).

Tontsch et al., "Isolation, Characterization, and Long–Term Cultivation of Porcine and Murine Cerebral Capillary Endothelial Cells", *Microvascular Res.,* 37:148–161 (1981).

Vogel et al., "Modulation of Endothelial Cell Proliferation, Adhesion, and Motility by Recombinant Heparin–Binding Domain and Synthetic Peptides From the Type I Repeats of Thrombospondin", *J. Cellular Biochem.,* 53:1–11 (1993).

Weiss et al., "Cellular and Subcellular Localization of the Bactericidal/Permeability–Increasing Protein of Neutrophils", *Blood,* 69(2):652–659 (Feb. 1987).

Weiss et al., *J. Biol. Chem.,* 253(8):2664–2672 (1978).

Weiss et al., "Partial Characterization and Purification of a Rabbit Granulocyte Factor that Increases Permeability of *Escheria coli", J. Clin. Invest.,* 55:33–42 (1975).

Yayon et al., "Cell Surface, Heparin–Like Molecules are Required for Binding of Basic Fibroblast Growth to its High Affinity Receptor", *Cell,* 64:641–648 (Feb. 22, 1991).

Yong et al.,"An Experimental Mouse Model of Yersinia–Induced Reactive Arthritis", *Microbial Pathogenesis,* 4:305–310 (1988).

Fig. 10

```
1                              I                                    50
|                           17-45                                    |
VNPGVVVRISQKGLDY|ASQQGTAALQKELKRIKIPDYSDSFKIKH|LGKGH

60                    II                           100
         |                   65-99                            |
YSFYSMDIREFQLP|SSQISMVPNVGLKFSISNANIKISGKWKAQKRFLK|M 110                                              150
       |                                                |
SGNFDLSIEGMSISADLKLGSNPTSGKPTITCSSCSSHINS|VHVHISKSK

III
      142-169                                          199
                                                         |
|VGWLIQLFHKKIESALRNK|MNSQVCEKVTNSVSSELQPYFQTLPVMTKI
```

Fig. 23

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( x i ) SEQUENCE DESCRIPTION: SEQ ID NO:1:

```
CAGGCCTTGA  GGTTTTGGCA  GCTCTGGAGG  ATG  AGA  GAG  AAC  ATG  GCC  AGG  GGC       54
                                    Met  Arg  Glu  Asn  Met  Ala  Arg  Gly
                                    -31  -30                           -25

CCT  TGC  AAC  GCG  CCG  AGA  TGG  GTG  TCC  CTG  ATG  GTG  CTC  GTC  GCC  ATA   102
Pro  Cys  Asn  Ala  Pro  Arg  Trp  Val  Ser  Leu  Met  Val  Leu  Val  Ala  Ile
               -20                      -15                     -10

GGC  ACC  GCC  GTG  ACA  GCG  GCC  GTC  AAC  CCT  GGC  GTC  GTG  GTC  AGG  ATC   150
Gly  Thr  Ala  Val  Thr  Ala  Ala  Val  Asn  Pro  Gly  Val  Val  Val  Arg  Ile
```

|  |  |  |  |  |  | −5 |  |  |  |  | 1 |  |  |  |  | 5 |  |  |
|---|---|---|---|---|---|---|---|---|---|---|---|---|---|---|---|---|---|---|

```
TCC  CAG  AAG  GGC  CTG  GAC  TAC  GCC  AGC  CAG  CAG  GGG  ACG  GCC  GCT  CTG       198
Ser  Gln  Lys  Gly  Leu  Asp  Tyr  Ala  Ser  Gln  Gln  Gly  Thr  Ala  Ala  Leu
 10                  15                  20                              25

CAG  AAG  GAG  CTG  AAG  AGG  ATC  AAG  ATT  CCT  GAC  TAC  TCA  GAC  AGC  TTT       246
Gln  Lys  Glu  Leu  Lys  Arg  Ile  Lys  Ile  Pro  Asp  Tyr  Ser  Asp  Ser  Phe
                     30                  35                              40

AAG  ATC  AAG  CAT  CTT  GGG  AAG  GGG  CAT  TAT  AGC  TTC  TAC  AGC  ATG  GAC       294
Lys  Ile  Lys  His  Leu  Gly  Lys  Gly  His  Tyr  Ser  Phe  Tyr  Ser  Met  Asp
               45                        50                  55

ATC  CGT  GAA  TTC  CAG  CTT  CCC  AGT  TCC  CAG  ATA  AGC  ATG  GTG  CCC  AAT       342
Ile  Arg  Glu  Phe  Gln  Leu  Pro  Ser  Ser  Gln  Ile  Ser  Met  Val  Pro  Asn
          60                        65                        70

GTG  GGC  CTT  AAG  TTC  TCC  ATC  AGC  AAC  GCC  AAT  ATC  AAG  ATC  AGC  GGG       390
Val  Gly  Leu  Lys  Phe  Ser  Ile  Ser  Asn  Ala  Asn  Ile  Lys  Ile  Ser  Gly
     75                        80                        85

AAA  TGG  AAG  GCA  CAA  AAG  AGA  TTC  TTA  AAA  ATG  AGC  GGC  AAT  TTT  GAC       438
Lys  Trp  Lys  Ala  Gln  Lys  Arg  Phe  Leu  Lys  Met  Ser  Gly  Asn  Phe  Asp
 90                       95                       100                      105

CTG  AGC  ATA  GAA  GGC  ATG  TCC  ATT  TCG  GCT  GAT  CTG  AAG  CTG  GGC  AGT       486
Leu  Ser  Ile  Glu  Gly  Met  Ser  Ile  Ser  Ala  Asp  Leu  Lys  Leu  Gly  Ser
                    110                      115                      120

AAC  CCC  ACG  TCA  GGC  AAG  CCC  ACC  ATC  ACC  TGC  TCC  AGC  TGC  AGC  AGC       534
Asn  Pro  Thr  Ser  Gly  Lys  Pro  Thr  Ile  Thr  Cys  Ser  Ser  Cys  Ser  Ser
               125                      130                      135

CAC  ATC  AAC  AGT  GTC  CAC  GTG  CAC  ATC  TCA  AAG  AGC  AAA  GTC  GGG  TGG       582
His  Ile  Asn  Ser  Val  His  Val  His  Ile  Ser  Lys  Ser  Lys  Val  Gly  Trp
          140                      145                      150

CTG  ATC  CAA  CTC  TTC  CAC  AAA  AAA  ATT  GAG  TCT  GCG  CTT  CGA  AAC  AAG       630
Leu  Ile  Gln  Leu  Phe  His  Lys  Lys  Ile  Glu  Ser  Ala  Leu  Arg  Asn  Lys
     155                      160                      165

ATG  AAC  AGC  CAG  GTC  TGC  GAG  AAA  GTG  ACC  AAT  TCT  GTA  TCC  TCC  AAG       678
Met  Asn  Ser  Gln  Val  Cys  Glu  Lys  Val  Thr  Asn  Ser  Val  Ser  Ser  Lys
170                      175                      180                      185

CTG  CAA  CCT  TAT  TTC  CAG  ACT  CTG  CCA  GTA  ATG  ACC  AAA  ATA  GAT  TCT       726
Leu  Gln  Pro  Tyr  Phe  Gln  Thr  Leu  Pro  Val  Met  Thr  Lys  Ile  Asp  Ser
                    190                      195                      200

GTG  GCT  GGA  ATC  AAC  TAT  GGT  CTG  GTG  GCA  CCT  CCA  GCA  ACC  ACG  GCT       774
Val  Ala  Gly  Ile  Asn  Tyr  Gly  Leu  Val  Ala  Pro  Pro  Ala  Thr  Thr  Ala
               205                      210                      215

GAG  ACC  CTG  GAT  GTA  CAG  ATG  AAG  GGG  GAG  TTT  TAC  AGT  GAG  AAC  CAC       822
Glu  Thr  Leu  Asp  Val  Gln  Met  Lys  Gly  Glu  Phe  Tyr  Ser  Glu  Asn  His
          220                      225                      230

CAC  AAT  CCA  CCT  CCC  TTT  GCT  CCA  CCA  GTG  ATG  GAG  TTT  CCC  GCT  GCC       870
His  Asn  Pro  Pro  Pro  Phe  Ala  Pro  Pro  Val  Met  Glu  Phe  Pro  Ala  Ala
     235                      240                      245

CAT  GAC  CGC  ATG  GTA  TAC  CTG  GGC  CTC  TCA  GAC  TAC  TTC  TTC  AAC  ACA       918
His  Asp  Arg  Met  Val  Tyr  Leu  Gly  Leu  Ser  Asp  Tyr  Phe  Phe  Asn  Thr
250                      255                      260                      265

GCC  GGG  CTT  GTA  TAC  CAA  GAG  GCT  GGG  GTC  TTG  AAG  ATG  ACC  CTT  AGA       966
Ala  Gly  Leu  Val  Tyr  Gln  Glu  Ala  Gly  Val  Leu  Lys  Met  Thr  Leu  Arg
                    270                      275                      280

GAT  GAC  ATG  ATT  CCA  AAG  GAG  TCC  AAA  TTT  CGA  CTG  ACA  ACC  AAG  TTC      1014
Asp  Asp  Met  Ile  Pro  Lys  Glu  Ser  Lys  Phe  Arg  Leu  Thr  Thr  Lys  Phe
               285                      290                      295

TTT  GGA  ACC  TTC  CTA  CCT  GAG  GTG  GCC  AAG  AAG  TTT  CCC  AAC  ATG  AAG      1062
Phe  Gly  Thr  Phe  Leu  Pro  Glu  Val  Ala  Lys  Lys  Phe  Pro  Asn  Met  Lys
          300                      305                      310

ATA  CAG  ATC  CAT  GTC  TCA  GCC  TCC  ACC  CCG  CCA  CAC  CTG  TCT  GTG  CAG      1110
Ile  Gln  Ile  His  Val  Ser  Ala  Ser  Thr  Pro  Pro  His  Leu  Ser  Val  Gln
```

-continued

|  |  | 315 |  |  |  | 320 |  |  |  | 325 |  |  |  |  |  |
|---|---|---|---|---|---|---|---|---|---|---|---|---|---|---|---|
| CCC | ACC | GGC | CTT | ACC | TTC | TAC | CCT | GCC | GTG | GAT | GTC | CAG | GCC | TTT | GCC | 1158
| Pro | Thr | Gly | Leu | Thr | Phe | Tyr | Pro | Ala | Val | Asp | Val | Gln | Ala | Phe | Ala |
| 330 |  |  |  |  | 335 |  |  |  |  | 340 |  |  |  |  | 345 |

GTC CTC CCC AAC TCC TCC CTG GCT TCC CTC TTC CTG ATT GGC ATG CAC  1206
Val Leu Pro Asn Ser Ser Leu Ala Ser Leu Phe Leu Ile Gly Met His
               350               355                   360

ACA ACT GGT TCC ATG GAG GTC AGC GCC GAG TCC AAC AGG CTT GTT GGA  1254
Thr Thr Gly Ser Met Glu Val Ser Ala Glu Ser Asn Arg Leu Val Gly
            365               370               375

GAG CTC AAG CTG GAT AGG CTG CTC CTG GAA CTG AAG CAC TCA AAT ATT  1302
Glu Leu Lys Leu Asp Arg Leu Leu Leu Glu Leu Lys His Ser Asn Ile
        380               385               390

GGC CCC TTC CCG GTT GAA TTG CTG CAG GAT ATC ATG AAC TAC ATT GTA  1350
Gly Pro Phe Pro Val Glu Leu Leu Gln Asp Ile Met Asn Tyr Ile Val
    395               400               405

CCC ATT CTT GTG CTG CCC AGG GTT AAC GAG AAA CTA CAG AAA GGC TTC  1398
Pro Ile Leu Val Leu Pro Arg Val Asn Glu Lys Leu Gln Lys Gly Phe
410               415               420               425

CCT CTC CCG ACG CCG GCC AGA GTC CAG CTC TAC AAC GTA GTG CTT CAG  1446
Pro Leu Pro Thr Pro Ala Arg Val Gln Leu Tyr Asn Val Val Leu Gln
                430               435               440

CCT CAC CAG AAC TTC CTG CTG TTC GGT GCA GAC GTT GTC TAT AAA       1491
Pro His Gln Asn Phe Leu Leu Phe Gly Ala Asp Val Val Tyr Lys
            445               450               455

TGAAGGCACC AGGGGTGCCG GGGGCTGTCA GCCGCACCTG TTCCTGATGG GCTGTGGGGC  1551

ACCGGCTGCC TTTCCCCAGG GAATCCTCTC CAGATCTTAA CCAAGAGCCC CTTGCAAACT  1611

TCTTCGACTC AGATTCAGAA ATGATCTAAA CACGAGGAAA CATTATTCAT TGGAAAAGTG  1671

CATGGTGTGT ATTTTAGGGA TTATGAGCTT CTTTCAAGGG CTAAGGCTGC AGAGATATTT  1731

CCTCCAGGAA TCGTGTTTCA ATTGTAACCA AGAAATTTCC ATTTGTGCTT CATGAAAAAA  1791

AACTTCTGGT TTTTTTCATG TG                                         1813

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Arg Glu Asn Met Ala Arg Gly Pro Cys Asn Ala Pro Arg Trp Val
-31     -30                 -25                 -20

Ser Leu Met Val Leu Val Ala Ile Gly Thr Ala Val Thr Ala Ala Val
-15                 -10                  -5                    1

Asn Pro Gly Val Val Val Arg Ile Ser Gln Lys Gly Leu Asp Tyr Ala
                 5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
50                  55                  60                  65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe

|   |   |   |   |   | 85 |   |   |   |   | 90 |   |   |   |   | 95 |   |   |
|---|---|---|---|---|---|---|---|---|---|---|---|---|---|---|---|---|---|
| Leu | Lys | Met 100 | Ser | Gly | Asn | Phe | Asp 105 | Leu | Ser | Ile | Glu | Gly 110 | Met | Ser | Ile |
| Ser | Ala 115 | Asp | Leu | Lys | Leu | Gly 120 | Ser | Asn | Pro | Thr | Ser 125 | Gly | Lys | Pro | Thr |
| Ile 130 | Thr | Cys | Ser | Ser | Cys 135 | Ser | Ser | His | Ile | Asn 140 | Ser | Val | His | Val | His 145 |
| Ile | Ser | Lys | Ser | Lys 150 | Val | Gly | Trp | Leu | Ile 155 | Gln | Leu | Phe | His | Lys 160 | Lys |
| Ile | Glu | Ser | Ala 165 | Leu | Arg | Asn | Lys | Met 170 | Asn | Ser | Gln | Val | Cys 175 | Glu | Lys |
| Val | Thr | Asn 180 | Ser | Val | Ser | Ser | Lys 185 | Leu | Gln | Pro | Tyr | Phe 190 | Gln | Thr | Leu |
| Pro | Val 195 | Met | Thr | Lys | Ile | Asp 200 | Ser | Val | Ala | Gly | Ile 205 | Asn | Tyr | Gly | Leu |
| Val 210 | Ala | Pro | Pro | Ala | Thr 215 | Thr | Ala | Glu | Thr | Leu 220 | Asp | Val | Gln | Met | Lys 225 |
| Gly | Glu | Phe | Tyr | Ser 230 | Glu | Asn | His | His | Asn 235 | Pro | Pro | Pro | Phe | Ala 240 | Pro |
| Pro | Val | Met | Glu 245 | Phe | Pro | Ala | Ala | His 250 | Asp | Arg | Met | Val | Tyr 255 | Leu | Gly |
| Leu | Ser | Asp 260 | Tyr | Phe | Phe | Asn | Thr 265 | Ala | Gly | Leu | Val | Tyr 270 | Gln | Glu | Ala |
| Gly | Val 275 | Leu | Lys | Met | Thr | Leu 280 | Arg | Asp | Asp | Met | Ile 285 | Pro | Lys | Glu | Ser |
| Lys 290 | Phe | Arg | Leu | Thr | Thr 295 | Lys | Phe | Phe | Gly | Thr 300 | Phe | Leu | Pro | Glu | Val 305 |
| Ala | Lys | Lys | Phe | Pro 310 | Asn | Met | Lys | Ile | Gln 315 | Ile | His | Val | Ser | Ala 320 | Ser |
| Thr | Pro | Pro | His 325 | Leu | Ser | Val | Gln | Pro 330 | Thr | Gly | Leu | Thr | Phe 335 | Tyr | Pro |
| Ala | Val | Asp 340 | Val | Gln | Ala | Phe | Ala 345 | Val | Leu | Pro | Asn | Ser 350 | Ser | Leu | Ala |
| Ser | Leu 355 | Phe | Leu | Ile | Gly | Met 360 | His | Thr | Thr | Gly | Ser 365 | Met | Glu | Val | Ser |
| Ala 370 | Glu | Ser | Asn | Arg | Leu 375 | Val | Gly | Glu | Leu | Lys 380 | Leu | Asp | Arg | Leu | Leu 385 |
| Leu | Glu | Leu | Lys | His 390 | Ser | Asn | Ile | Gly | Pro 395 | Phe | Pro | Val | Glu | Leu 400 | Leu |
| Gln | Asp | Ile | Met 405 | Asn | Tyr | Ile | Val | Pro 410 | Ile | Leu | Val | Leu | Pro 415 | Arg | Val |
| Asn | Glu | Lys 420 | Leu | Gln | Lys | Gly | Phe 425 | Pro | Leu | Pro | Thr | Pro 430 | Ala | Arg | Val |
| Gln | Leu 435 | Tyr | Asn | Val | Val | Leu 440 | Gln | Pro | His | Gln | Asn 445 | Phe | Leu | Leu | Phe |
| Gly 450 | Ala | Asp | Val | Val | Tyr 455 | Lys |   |   |   |   |   |   |   |   |   |

THERAPEUTIC USES OF BACTERICIDAL/ PERMEABILITY INCREASING PROTEIN (BPI) PROTEIN PRODUCTS

This is a divisional of U.S. patent application Ser. No. 08/415,158 filed Mar. 31, 1995, now U.S. Pat. No. 5,639,727, which is a file-wrapper-continuation of U.S. patent application Ser. No. 08/093,202 filed Jul. 15, 1993, abandoned, which is a continuation-in-part of U.S. patent application Ser. No. 08/030,644 filed Mar. 12, 1993, now U.S. Pat. No. 5,348,942.

BACKGROUND OF THE INVENTION

The present invention relates to therapeutic uses of bactericidal/permeability increasing (BPI) protein products for the treatment of conditions related to gram-negative bacterial infection and the conditions not directly associated with gram-negative bacterial infection, including neutralization of the anti-coagulant properties of heparin, inhibition of angiogenesis, tumor and endothelial cell proliferation and treatment of chronic inflammatory disease states such as arthritis.

Heparin Binding

Heparin is a heterogenous group of straight-chain anionic mucopolysaccharides, called glycosaminoglycans having anticoagulant properties. Although others may be present, the main sugars occurring in heparin are: (1) α-L-iduronic acid 2-sulfate, (2) 2-deoxy-2-sulfamino-α-D-glucose 6-sulfate, (3) β-D-glucuronic acid, (4) 2-acetamido-2-deoxy-α-D-glucose, and (5) α-L-iduronic acid. These sugars are present in decreasing amounts, usually in the order (2)>(1)>(4)>(3)>(5), and are joined by glycosidic linkages, forming polymers of varying sizes. Heparin is strongly acidic because of its content of covalently linked sulfate and carboxylic acid groups. Heparin is found within mast cell granules and is released upon degranulation. A cell associated form of heparin is termed heparan sulfate. Heparan sulfate is a broad term used to describe a variety of sulfated proteoglycans (HSPG's) found with a near-ubiquitous distribution on mammalian cell surface membranes and in the extracellular matrix. HSPG contains a variable percentage of pentameric heparin-like sequences that function in a similar fashion as soluble heparin. The HSPG's serve as a repository for antithrombin III (ATIII) and for heparin-binding growth factors such as fibroblast growth factors (FGF) 1–5, IL-8, GM-CSF and IL-3. Folkman et al., *Inflammation: Basic Principles and Clinical Correlates*, 2d Ed. Chapter 40, pp 821–839 (1992). In fact, cells made genetically deficient in HSPG's require exogenous heparin for growth.

Heparin is commonly administered in doses of up to 400 U/kg during surgical procedures such as cardiopulmonary bypass, cardiac catheterization and hemodialysis procedures in order to prevent blood coagulation during such procedures. The anticoagulant effect of heparin in blood is a result of the interaction of heparin with ATIII. The heparin/ATIII complex is a potent inhibitor of many of the clotting factors of the coagulation cascade. Specific inhibition has been demonstrated for activated Factors IXa, Xa, XIa, XIIIa and thrombin. The heparin/ATIII complex has the highest affinity for Factor Xa and thrombin which are common to both the intrinsic and extrinsic clotting pathways involved as the last two steps of the clotting cascade that results in the conversion of fibrinogen to fibrin.

When heparin is administered for anticoagulant effects during surgery, it is an important aspect of post-surgical therapy that the effects of heparin are promptly neutralized so that normal coagulation function can be restored. Currently protamine is used to neutralize heparin. Protamines are simple proteins of low molecular weight which are commonly isolated from salmon sperm. They are rich in arginine amino acid residues and strongly basic. Administered alone, protamines (usually in the form of protamine sulfate) have anti-coagulant effects. When administered in the presence of heparin, a stable complex is formed and the anticoagulant activity of both drugs is lost. Significant hypotensive and anaphylactoid effects of protamine have limited its clinical utility.

Other reported compounds which have heparin neutralizing activity include platelet factor 4 (PF4) and major basic protein, see U.S. Pat. No.5,086,164. Major basic protein demonstrates heparin neutralizing activity but is also highly toxic.

Angiogenesis

Angiogenesis is closely associated with endothelial cell proliferation and constitutes the development of new capillary blood vessels. As such, it is an important process in mammalian development and growth, and in menstruation processes. The release of angiogenic growth factors, such as fibroblast growth factors 1–5, induces proliferation of endothelial cells via a heparin-dependent receptor binding mechanism. See Yayon et al., *Cell,* 64:841–848 (1991). These heparin-binding growth factors can be released due to vascular trauma (wound healing), immune stimuli (autoimmune disease), inflammatory mediators (prostaglandins) and from tumor cells.

Angiogenesis is also associated with a number of pathological conditions in which it would be desirable to inhibit such new blood vessel development. As one example, angiogenesis is critical to the growth, proliferation, and metastasis of various tumors. Other pathological conditions associated with angiogenesis include diabetic retinopathy, retrolental fibroplasia, neovascular glaucoma, psoriasis, angiofibromas, immune and non-immune inflammation including rheumatoid arthritis, capillary proliferation within atherosclerotic plaques, hemangiomas, endometriosis and Kaposi's Sarcoma.

Folkman et al., supra, discloses that psoriatic lesions in the skin are dominated by epithelial proliferation, neovascularization, and an infiltrate of inflammatory cells. It is unclear, however, whether angiogenesis is a step in the pathogenesis of psoriasis or a secondary phenomenon.

Several substances are known to function as angiogenesis inhibitors and have been reported to inhibit tumor angiogenesis, to prevent the onset of arthritis and to inhibit established arthritis in collagen-induced arthritis models, Peacock et al., *J. Exp. Med.,* 175, 1135–1138 (1992). As one example, protamine is known to inhibit tumor angiogenesis and subsequent tumor growth. According to Taylor et al., *Nature,* 297:307–312 (1982) protamine's anti-angiogenic activity is attributed to is ability to bind heparin. PF4 is also known to exhibit anti-angiogenic activity. Of interest to the present application is U.S. Pat. No. 5,112,946 which discloses modified PF4 and analogs thereof which have anti-angiogenic activity but lack the ability to bind heparin. PF4 has been shown to have at least two functional properties. Heparin binding has been studied most extensively; however, PF4 was originally described to have collagenase inhibitory properties. Collagenase inhibitors were the first inhibitors of angiogenesis to be discovered. See Folkman, 1973, supra. The mutations in the heparin binding region of PF4 were not examined for their effect on collagenase inhibitory activity. Interestingly, thrombospondin is also an inhibitor of angiogenesis and binds to heparin with a serine/tryptophan motif instead of a basic amino acid motif. Thus, there is no obvious single consensus sequence heparin binding or for angiogenesis inhibition.

PCT. publication number WO 92/01003 discloses the use of glycosaminoglycan (heparin) derivatives and their use as inhibitors of tumor invasiveness. Heparin derivatives are disclosed which are described as being substantially devoid of anticoagulation activity and which impede the formation of tumor metastases in a host.

Chronic Inflammation

Chronic inflammation is usually accompanied by angiogenesis. Arthritis is a chronic syndrome characterized by the inflammation of the peripheral joints accompanied by synovial thickening and the influx of immune factors and cells such as polymorphonuclear leukocytes (PMN). In rheumatoid arthritis, the inflammation is immune driven, while in reactive arthritis, inflammation is associated with infection of the synovial tissue with pyogenic bacteria or other infectious agents. Folkman et al., 1973, supra, also note that many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease, and not an epiphenomenon, there is evidence that angiogenesis is necessary for the maintenance of synovitis in rheumatoid arthritis. While nonsteroidal anti-inflammatory drugs (NSAIDs), corticosteroids and other therapies have provided improvements in relief for treatment of arthritis, there remains a need in the art for more effective therapies for arthritis and other inflammatory diseases.

Inflammation and angiogenesis are now understood to be separable but not mutually exclusive processes. Specific angiogenic proteins have been discovered that stimulate angiogenesis without inflammation whereas angiostatic steroids can inhibit angiogenesis without decreasing acute inflammation. See Folkman, 1973, supra. Interestingly, endotoxin has been identified as the most potent exogenous stimulator of angiogenesis through its stimulation of macrophage cytokines and growth factors.

Bactericidal/Perimeability-Increasing Protein

Bactericidal/permeability-increasing protein (BPI) is a protein isolated from the granules of mammalian PMNs, which are blood cells essential in the defense against invading microorganisms. Human BPI protein has been isolated from polymorphonuclear neutrophils by acid extraction combined with either ion exchange chromatography [Elsbach, *J. Biol. Chem.*, 254:11000 (1979)] or *E. coli* affinity chromatography [Weiss, et al., *Blood*, 69:652 (1987)], referred to herein as natural BPI, and has potent bactericidal activity against a broad spectrum of gram-negative bacteria. The molecular weight of human BPI is approximately 55,000 daltons (55 kD). The amino acid sequence of the entire human BPI protein, as well as the DNA encoding the protein, have been elucidated in FIG. 1 of Gray et al., *J. Biol. Chem.*, 264:9505 (1989), incorporated herein by reference.

The bactericidal effect of BPI has been shown to be highly specific to sensitive gram-negative species, while non-toxic for other microorganisms and for eukaryotic cells. The precise mechanism by which BPI kills bacteria is as yet unknown, but it is known that BPI must first attach to the surface of susceptible gram-negative bacteria. This initial binding of BPI to the bacteria involves electrostatic interactions between the basic BPI protein and the negatively charged sites on lipopolysaccharides (LPS). LPS has been referred to as "endotoxin" because of the potent inflammatory response that it stimulates. LPS induces the release of mediators by host inflammatory cells which may ultimately result in irreversible endotoxic shock. BPI binds to lipid A, the most toxic and most biologically active component of LPS.

In susceptible bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. Elsbach and Weiss, *Inflammation: Basic Principles and Clinical Correlates,* eds. Gallin et al., Chapter 30, Review Press, Ltd. (1992). BPI is thought to act in two stages. The first is a sublethal stage that is characterized by immediate growth arrest, permeabilization of the outer membrane and selective activation of bacterial enzymes that hydrolyze phospholipids and peptidoglycan. Bacteria at this stage can be rescued by plating on serum albumin supplemented media. The second stage, defined by growth inhibition that cannot be reversed by serum albumin, occurs after prolonged exposure of the bacteria to BPI and is characterized by extensive physiologic and structural changes, including penetration of the cytoplasmic membrane.

BPI is also capable of neutralizing the endotoxic properties of LPS to which it binds. Because of its gram-negative bactericidal properties and its ability to neutralize LPS, BPI can be utilized for the treatment of mammals suffering from diseases caused by gram-negative bacteria, such as bacteremia or sepsis.

A proteolytic fragment corresponding to the N-terminal portion of human BPI holoprotein possesses the lipid A binding and antibacterial activity of the naturally-derived 55 kD human holoprotein. In contrast to the N-terminal portion, the C-tenninal region of the isolated human BPI protein displays only slightly detectable anti-bacterial activity. Ooi, et al., *J. Exp. Med.*, 174:649 (1991). A BPI N-terminal fragment, comprising approximately the first 199 amino acid residues of the human BPI holoprotein and referred to as "rBPI$_{23}$", has been produced by recombinant means as a 23 kD protein. Gazzano-Santoro et al., *Infect. Immun.* 60:4754–4761 (1992).

Of interest to the present application are the disclosures in PCT International Application PCT/US91/05758 having publication No. WO 92/03535 relating to compositions comprising a BPI protein and an anionic compound which compositions are said to exhibit (1) no bactericidal activity and (2) endotoxin neutralizing activity. Anionic compounds are preferably a protein such as serum albumin but can also be a proteoglycan such as heparin. In addition, Weiss et al., *J. Clin. Invest.*, 55:33–42 (1975) discloses that heparin sulfate and LPS bind to block expression of the permeability increasing activity of BPI. Neither reference discloses neutralization of heparin by combination with BPI, however.

There continues to exist a need in the art for new products and methods for use in neutralization of heparin, inhibition of tumor and angiogenesis, endothelial cell proliferation and treatment of chronic inflammation.

SUMMARY OF THE INVENTION

According to one aspect of the invention, methods are provided for neutralizing the anti-coagulant activity of heparin comprising administering an effective amount of a BPI protein product in vivo to a subject or in vitro to a fluid sample containing heparin.

According to another aspect of the invention, a BPI protein product is administered to subjects in order to inhibit endothelial cell proliferation including but not limited to endothelial cell proliferation associated with angiogenesis.

The invention provides methods of inhibiting angiogenesis associated with a variety of clinical conditions. Specifically provided by the invention are methods of treating cancer by inhibiting angiogenesis associated with malignant tumor proliferation; Kaposi's sarcoma lesions and the like. Cancers susceptible to treatment by administration of BPI protein products include melanoma, sarcomas, and carcinomas including but not limited to breast, colon, lung, and prostate carcinomas. Other conditions for which BPI protein products can be administered for inhibition of angiogenesis include ocular retinopathy, retrolental fibroplasia, psoriasis, angiofibromas, endometriosis, hemangiomas and the like. Also contemplated by the invention are methods of contraception comprising delivering of an effective amount of a BPI protein product so as to prevent implantation of a fertilized ovum.

The invention also provides methods of treating chronic inflammatory disease states such as arthritis, psoriasis, inflammatory bowel disease, Crohn's disease, ulcerative colitis, lupus erythematosus, autoimmune uveitis, Lyme disease, and asthma comprising administering an effective amount of a BPI protein product to a subject suffering from the inflammatory disease state.

The invention also provides methods of preparation of medicaments for neutralization of the anti-coagulant properties of heparin, inhibition of tumor and endothelial cell proliferation, inhibition of angiogenesis and treatment of chronic inflammatory disease states.

Such medicaments can be prepared for oral administration for injection or other parenteral methods and preferably include conventional pharmaceutically acceptable carriers and adjuvants as would be known to those of skill in the art. The medicaments are preferably in the form of a unit dose in solid, semi-solid and liquid dosage forms such as tablets, pills, powders, liquid solutions or suspensions, and injectable and infusible solutions. Effective dosage ranges from about 100 $\mu$g/kg to about 10 mg/kg of body weight are contemplated.

As used herein, "BPI protein product" includes naturally and recombinantly produced bactericidal/permeability-increasing protein; natural, synthetic, and recombinant biologically active polypeptide fragments of bactericidal/permeability increasing protein; and biologically active polypeptides or analogs, including hybrid fusion proteins, of either bactericidal/permeability increasing protein or biologically active fragments thereof.

BRIEF DESCRIPTION OF THE FIGURES

FIG. 10 depicts a graph showing the effect of rBPI$_{23}$ on inhibition of *Borrelia burgdorferi* LPS-like stimulation of the LAL assay;

FIG. 23 depicts the functional domains of rBPI$_{23}$ (amino acids 1–199 of SEQ ID NO: 2).

DETAILED DESCRIPTION

Figure 1:
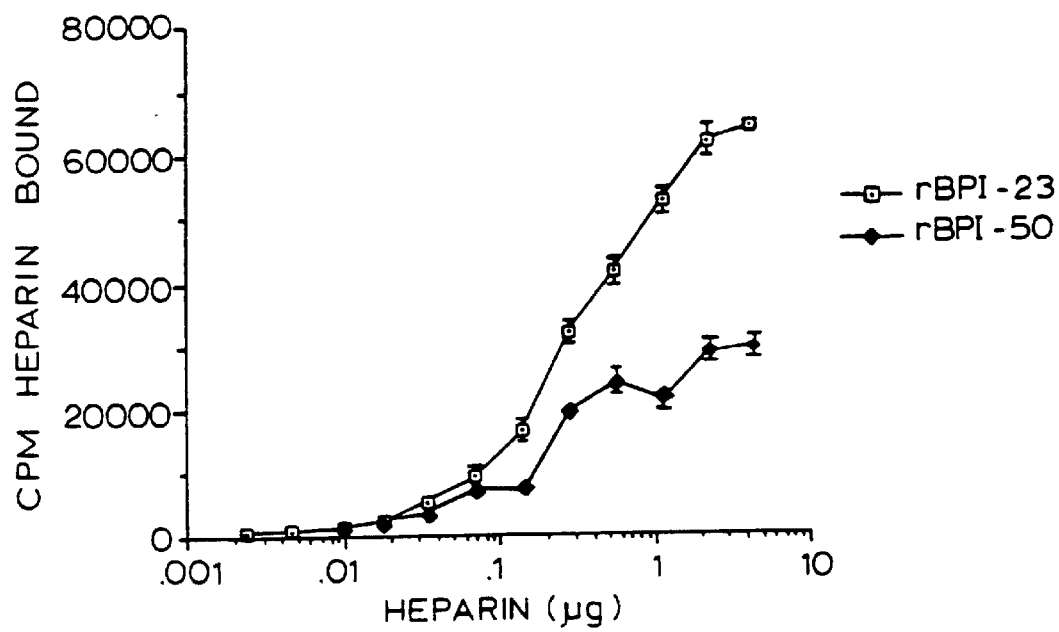
FIG. 1 depicts a graph of a heparin binding assay for rBPI$_{23}$ and rBPI.

The present invention relates to the administration of bactericidal/permeability-increasing protein (BPI) protein products for the treatment of a variety of therapeutic conditions not directly associated with bacterial infection.

While BPI protein products as described herein are useful as potent cytotoxins for gram-negative bacteria and for neutralizing the adverse effects of lipopolysaccharide associated with the cell walls of gram-negative bacteria, a variety of therapeutic effects for BPI protein products not directly associated with the gram-negative bacterial infection have been discovered. Specifically, the invention provides methods for treating conditions not directly associated with gram-negative infections including neutralization of the anti-coagulant activity of heparin, inhibition of tumor and endothelial cell proliferation including cell proliferation associated with angiogenesis and treatment of chronic inflammatory disease states such as arthritis.

The BPI protein products including biologically active fragments of BPI holoprotein which are to be administered according to the methods of this invention may be generated and/or isolated by any means known in the art. U.S. Pat. No. 5,439,807, hereby incorporated by reference, discloses novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI include biologically active molecules that contains the same amino acid sequence as a BPI holoprotein, except that the molecule lacks amino-terminal amino acids, internal amino acids, and/or carboxy-terminal amino acids of the holoprotein. By way of nonlimiting examples, such fragments include those described herein and the previously mentioned natural 25 kD fragment and a recombinant 23 kD, 199 amino acid residue amino-terminal fragment of the human BPI holoprotein referred to as $rBPI_{23}$. See, Gazzano-Santoro et al., Infect. Immun. 60:4754–4761 (1992). In that publication, an expression vector was used as a source of DNA encoding a recombinant expression product ($rBPI_{23}$) having the 31-residue signal sequence and the first 199 amino acids of the N-terminus of the mature human BPI, as set out in SEQ ID NOs: 1 and 2 taken from Gray et al., supra, except that valine at position 151 is specified by GTG rather than GTC and residue 185 is glutamic acid (specified by GAG) rather than lysine (specified by AAG). Recombinant holoprotein referred to herein as rBPI or $rBPI_{50}$ has also been produced having the sequence set out in SEQ ID NOs: 1 and 2 taken from Gray et al., supra, with the exceptions noted for $rBPI_{23}$.

Other non-limiting examples of biologically active fragments of BPI include fragments of, e.g., the BPI holoprotein or of $rBPI_{23}$ generated upon subjecting the proteins to chemical cleavage with agents such as cyanogen bromide (CNBr) or enzymatic digestion with agents such as endoproteinase Asp-N. BPI protein fragments may also be provided in the form of linear or cyclic synthetic peptides comprising replicas of from about 5 to about 50 continuous amino acids within the BPI holoprotein and especially within the amino terminal half of the protein. Such peptides may be provided in monomeric form, in the form of dimers or multimers (where the peptide replicates a region of BPI having cysteine residues) and in the form of "linear" dimers or multimers wherein a BPI sequence is present repeatedly in the peptide, with or without separation by "spacer" amino acids allowing for selected conformational presentation.

Biologically active analogs of BPI include but are not limited to recombinant hybrid fusion proteins comprising BPI holoprotein or biologically active fragment thereof, and at least a portion of at least one other polypeptide. Such proteins are described by Theofan et al. in U.S. Pat. No. 5,439,807, incorporated herein by reference in their entirety and include hybrid fusion proteins comprising, at the amino terminal end, a BPI protein or a biologically active fragment thereof and, at the carboxy terminal end, at least one constant domain of an immunoglobulin heavy chain or allelic variant thereof.

Biologically active analogs of BPI also include but are not limited to BPI protein products wherein one or more amino acid residues has been replaced by a different amino acid or by atypical amino acids. For example, U.S. Pat. No. 5,420, 019, which is incorporated herein by reference, discloses polypeptide analogs of BPI and BPI fragments wherein a cysteine residue at position 132 or at position 135 is replaced by a different amino acid. One preferred protein product designated $rBPI_{23}{}^{\Delta}$ cys comprises the first 199 amino acid residues of BPI holoprotein but wherein the cysteine residue at position 132 is substituted with an alanine U.S. Ser. No. 08/013,801, now U.S. Pat. No. 5,420,019, also discloses N-terminal fragments of BPI protein having molecular weights of approximately 21 KD.

The administration of BPI protein products is preferably accomplished with a pharmaceutical composition comprising a BPI protein product and a pharmaceutically acceptable diluent, adjuvant, or carrier. The BPI protein product composition may be administered without or in conjunction with known antibiotics, surfactants, or other chemotherapeutic agents. A preferred pharmaceutical composition containing BPI protein products comprises BPI at a concentration of 1 mg/ml in citrate buffered saline (0.02M citrate, 0.15M NaCl, pH 5.0) comprising 0.1% by weight of poloxamer 188 (PLURONIC F-68, BASF Wyandotte, Parsippany, N.J.) and 0.002% by weight of polysorbate 80 (TWEEN 80, ICI Americas Inc., Wilmington, Del.). Such preferred combinations are described in co-owned, copending, U.S. patent application Ser. No.08/012,360 (McGregor et al., "Improved Pharmaceutical Composition"), filed Feb. 2, 1993, the disclosure of which is incorporated herein by reference.

Effective doses of BPI and BPI protein products for partial or complete neutralization of the anti-coagulant activity of heparin and other effects described herein may be readily determined by those of skill in the art according to conventional parameters including the size of the subject, the quantity of heparin administered to the subject and the time since administration of the heparin.

Other aspects and advantages of the present invention will be understood upon consideration of the following illustrate examples. Example 1 addresses assay systems for quantification of heparin binding by BPI protein products; Example 2 describes the relative capacity of heparin to block binding of bacterial LPS to BPI protein products; Examples 3 and 4, respectively, present results of tests for the capacity of BPI protein products to inhibit thrombin or Factor Xa inactivation by antithrombin III/heparin complexes; and Example 5 relates to the effect of BPI protein products on heparin-mediated lengthening of thrombin time. Example 6 relates to the effect of BPI protein products on heparin mediated lengthening of partial thromboplastin time. Examples 7–9 relate to administration of BPI protein products in model systems of in collagen and bacterial induced arthritis animal model systems exemplifying treatment of chronic inflammatory disease states. Examples 10–11 illustrate testing of BPI protein products for angiostatic effects in a mouse malignant melanoma metastasis model system. Example 12 addresses effects of BPI protein products on endothelial cell proliferation and possible binding mechanisms involved. Example 13 relates to preparation of synthetic BPI peptides. Examples 14–16 illustrate heparin-binding, LPS-binding and bactericidal activities for the synthetic BPI peptides of Example 13. Example 17 relates to preparation of additional synthetic BPI peptides. Examples 18 through 21 address properties of the peptides of Example 17. Example 22 discloses the preparation of BPI proteolytic fragment peptides. Example 23 discloses the bactericidal effects of the BPI proteolytic fragments. Example 24 discloses the heparin binding properties of the BPI proteolytic fragments. Example 25 discloses the effect of BPI proteolytic fragments on an LAL assay.

EXAMPLE 1

HEPARIN BINDING BY BPI PROTEIN PRODUCTS

Heparin binding assays were conducted using membrane bound natural and recombinant BPI molecules and radiolabelled heparin. Briefly, rBPI$_{23}$ and holoprotein designated rBPI or rBPI$_{50}$ were added to wells of a 96-well microtiter plate having an Immobilon-P (Millipore, Bedford, Mass.) membrane disposed at the bottom of the wells. Five µg of protein was added to each well. The wells were dried and subsequently blocked with a 0.1% bovine serum albumin (BSA) in phosphate buffered saline, pH 7.4 (blocking buffer.) Dilutions of $^3$H-heparin (DuPont, NEN, Wiulmington, Del.) were made in the blocking buffer and incubated in the BPI containing wells for one hour at 4° C. The unbound heparin is aspirated and the wells were washed three times with blocking buffer, dried and removed for quantitation in a liquid scintillation counter. Typical assay results are graphically presented in FIG. 1. While BSA in the blocking buffer does have a low affinity and capacity to bind heparin, this was considered physiologically irrelevant and the background was routinely subtracted from the test compound signal. The binding of radiolabeled heparin was completely inhibited by a 100 fold excess of unlabeled heparin (data not shown).

Similar assays compared heparin binding by rBPI$_{23}$, rBPI$_{50}$, and natural holoprotein (BPI) with thaumatin control protein (having charge and size similar to rBPI$_{23}$) or with a wash buffer (1% BSA) control. In these assays, less heparin binding by the natural and recombinant BPI holoproteins was observed. The lesser extent of binding by rBPI and nBPI may have been the result of carbohydrate contamination of the protein preparations.

In addition, binding constants with $^3$H-heparin as the ligand were determined using nonlinear function minimization with GRAFIT software (Erithicus Software Ltd., Staines, UK) for rBPI$_{23}$, rBPI, protamine sulfate (Sigma Chemical Co.) and thaumatin with the results shown in Table 1 below.

TABLE 1

Binding Constants with $^3$H-heparin as the Ligand

| PROTEIN | K$_d$ | CAPACITY | HEPARIN COLUMN NaCl ELUTION |
|---|---|---|---|
| rBPI$_{23}$ | 79 nM | 2.63 µg | 0.84 M |
| rBPI$_{50}$ | 173 nM | 1.30 µg | 0.81 M |
| Protamine | 8.1 nM | 2.66 µg | 1.33 M |
| Thaumatin | no binding | | 0.15 M |

EXAMPLE 2

HEPARIN COMPETITION FOR BPI PROTEIN PRODUCT BINDING

Figure 2:
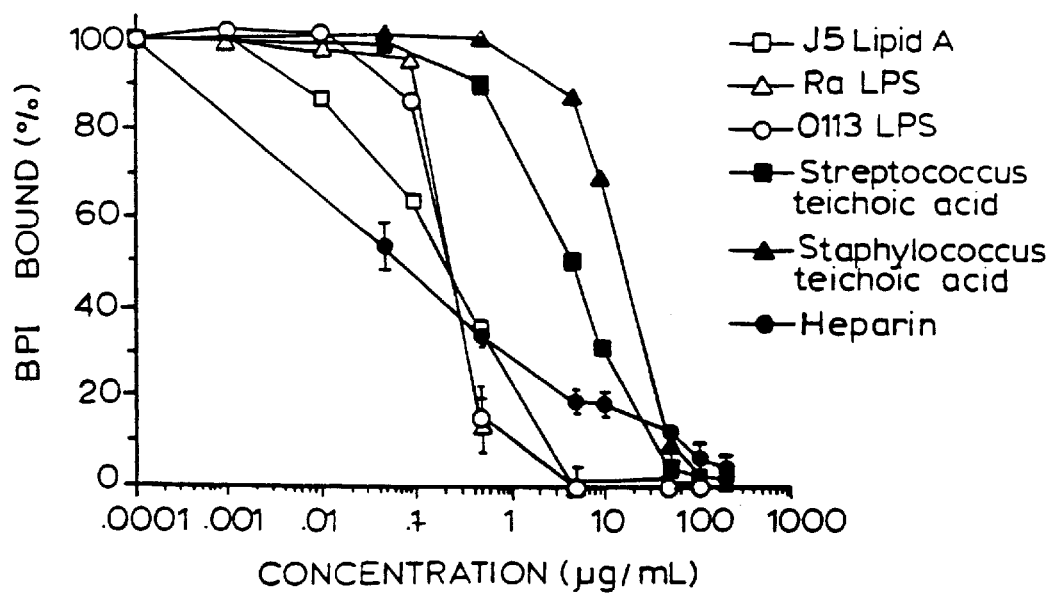
FIG. 2 depicts a graph showing the effect of heparin on rBPI$_{23}$ binding to *E. coli* J5 lipid A compared to various LPS and teichoic acid samples.

The ability of heparin, soluble lipid A, LPS, and Teichoic acids to compete with immobilized E. coli J5 lipid A for binding to soluble rBPI$_{23}$ was assessed. Specifically, IMMULON 2 (Dynatech, Chantilly, Va.) microtiter wells were coated with E. coli J5 lipid A at a concentration of 0.5 µg/mL in methanol (50 µL volume). The wells were then blocked for 4 hours at 37° C. with PBS containing 0.1% BSA. Control wells were treated with 50 µL of plain methanol and then blocked as above. The blocked wells were aspirated and washed twice with PBS0.05% TWEEN-20. Varying concentrations of putative inhibitors were plated onto the wells in a volume of 25 µL PBS, followed by 200,000 cpm of radio-iodinated rBPI$_{23}$ in 25 µL of PBS containing 0.1% TWEEN-20. The test solutions included Ra LPS from *Salmonella minnesota* R60 at 200 µg/mL; smooth LPS from *E. coli* 0113 (RIBI Immunochem, Hamilton, Mont., #R318) at 200 µg/mL; lipoteichoic acid from *Streptococcus faecalis*, (Sigma, St. Louis, Mo., #L-4015) at 400 µg/mL; lipoteichoic acid from *Staphylococcus Aureus*, (Sigma #L-2525) at 400 µg/mL; and heparin sodium USP injection (Lypho-Med, Rosemont, Ill., #9155-01) at 400 µg/mL. Binding was allowed to proceed overnight at 4° C. with gentle shaking, after which the wells were aspirated, washed three times with PBS/0.05 % TWEEN-20, and counted. The results as set out in FIG. 2 show a high affinity of rBPI$_{23}$ for heparin and also that heparin blocks BPI binding to lipid A.

EXAMPLE 3

HEPARIN NEUTRALIZATION BY BPI PROTEIN PRODUCTS: EFFECT OF BPI ON THROMBIN INACTIVATION BY ATIII/HEPARIN COMPLEXES

A chromogenic assay was used to determine the effect of rBPI$_{23}$ on thrombin inactivation by ATIII heparin complexes. Specifically, a Chromostrate™ anti-thrombin assay kit (Organon Teknika Corp., Durham, N.C.) was used to examine the inhibition of purified thrombin by performed ATIII/heparin complexes in plasma.

Figure 3:
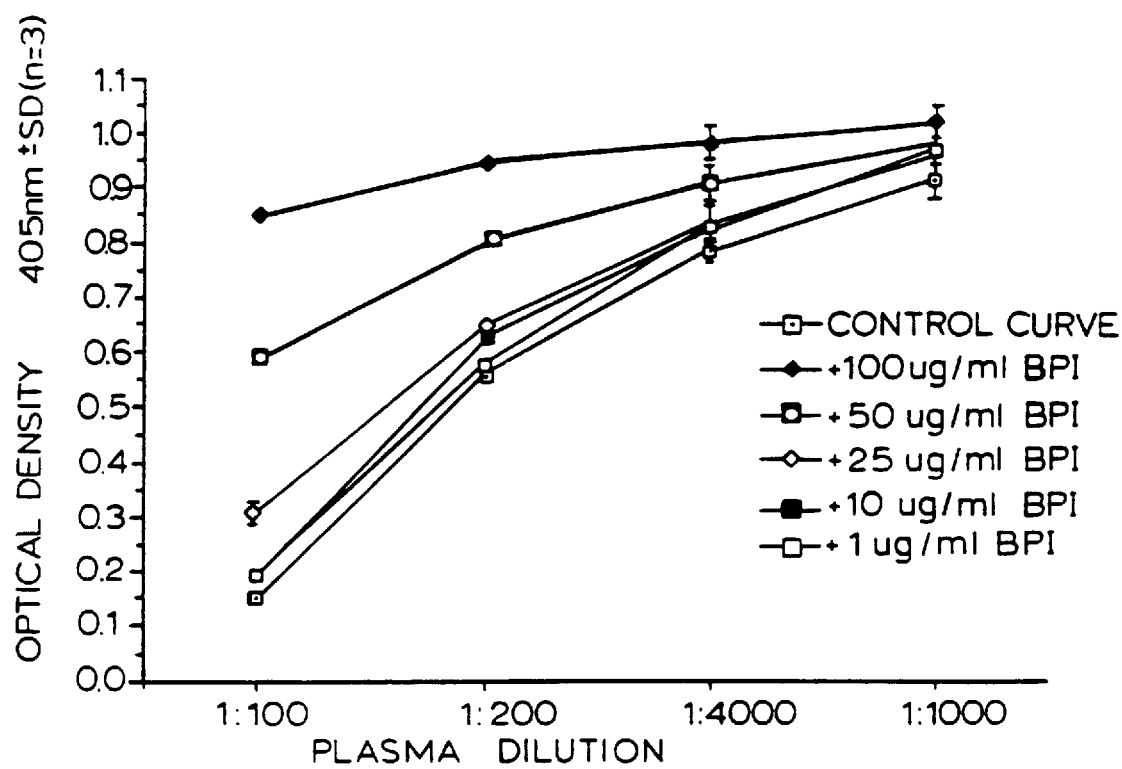
FIG. 3 depicts a graph showing the effect of rBPI$_{23}$ on ATIII/heparin inhibition of thrombin.

The assay was performed in 96 well microtiter plates in triplicate with a final volume per well of 200 µL. The order of addition of assay components was as follows: 1) 50 µl sample (rBPI$_{23}$ or thaumatin as a control protein) with final concentrations of 100, 50, 25, 10 and 1 µg/well in PBS; 2) 50 µl plasma 1:100 in buffer; 3) 50 µl thrombin at 1 nKat/mL in buffer; and 4) 50 µl chromogenic substrate 1 µmol/mL in H$_2$O. The reaction was allowed to proceed for 10 minutes at 37° C. and stopped with 50 µL 0.1M citric acid and the color reaction was quantitated on a microplate reader. The assay results shown in FIG. 3 indicate that rBPI$_{23}$ can effectively neutralize ATIII/heparin complexes in heparinized human plasma in a dose dependent manner. As the plasma was titrated the amount of thrombin activity increased. This was caused by a decrease in the amount of inhibitory ATIII/heparin complexes in the added plasma. The control protein, thaumatin, showed no similar neutralizing effect and was essentially equivalent to the buffer control at all protein concentrations.

EXAMPLE 4

HEPARIN NEUTRALIZATION BY BPI PROTEIN PRODUCTS: EFFECT OF BPI ON FACTOR Xa INACTIVATION BY ATIII/HEPARIN COMPLEXES

A chromogenic assay was used to determine the effect of rBPI$_{23}$ on Factor Xa neutralization by ATIII/heparin complexes. Specifically, the assay was conducted using a chromostrate heparin anti-Factor Xa assay kit (Organon Teknika Corp.) and was performed under fixed concentrations of Factor Xa and ATIII. Heparin concentration was varied so that a heparin standard curve was generated for heparin at concentrations of 1, 0.5, 0.25, 0.125, 0.063, 0.031, 0.016, 0.008, 0.004, 0.002, and 0 units/mL in PBS. The assay measured functional Factor Xa activity by the release of a chromogenic compound from a synthetic substrate. ATIII/heparin complexes neutralize Factor Xa activity, thus the amount of chromogen released was inversely related to the amount and anti-Factor Xa activity of heparin in the assay sample.

Figure 4:
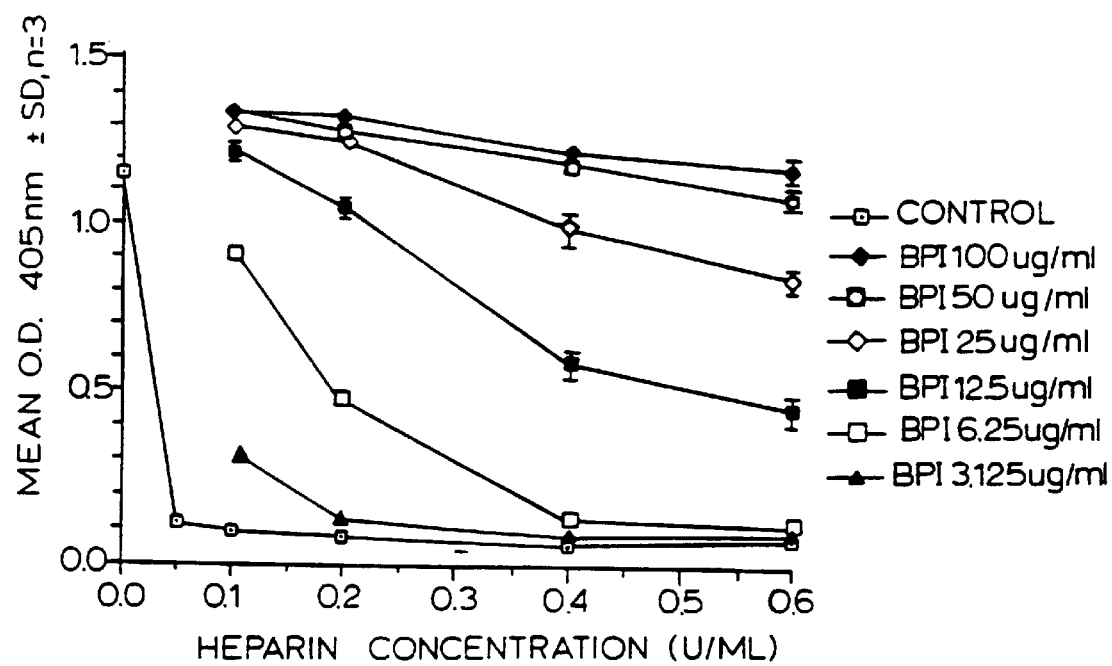
FIG. 4 depicts a graph showing the effect of rBPI$_{23}$ on ATIII/heparin inhibition of Factor Xa.

The assay was performed in 96 well microtiter plates in triplicate with a final volume per well of 200 μL. Assay components were added to the microtiter wells as follows: 1) 50 μL samples (rBPI$_{23}$ or thaumatin as a control protein) with final concentrations of 100, 50, 25, 10 and 1 μg/well in PBS; 2) 50 μL Factor Xa 0.14 nKat/mL in H$_2$O; 3) 25 μL ATIII at 0.5 U/mL in H$_2$O; 4) 24 μL heparin at 0.25 U/mL in buffer; 5) 50 μL substrate (3 μmoles/mL). The reaction was allowed to proceed for 10 minutes at 37° C. and stopped with 50 μl of 0.1M citric acid and then the color reaction was quantitated on a microplate reader. The assay results shown in FIG. 4 indicates that rBPI$_{23}$ can effectively neutralize heparin in the ATIII/heparin inhibition of Factor Xa. As the concentration of heparin is increased, the amount of rBPI$_{23}$ necessary for heparin neutralization also increased. The control protein, thaumatin, showed no similar neutralizing effects and was essentially equivalent to the buffer control at all protein concentrations.

EXAMPLE 5

HEPARIN NEUTRALIZATION BY BPI PROTEIN PRODUCTS: EFFECT OF BPI ON HEPARIN-MEDIATED LENGTHENING OF THROMBIN TIME

Figure 5:
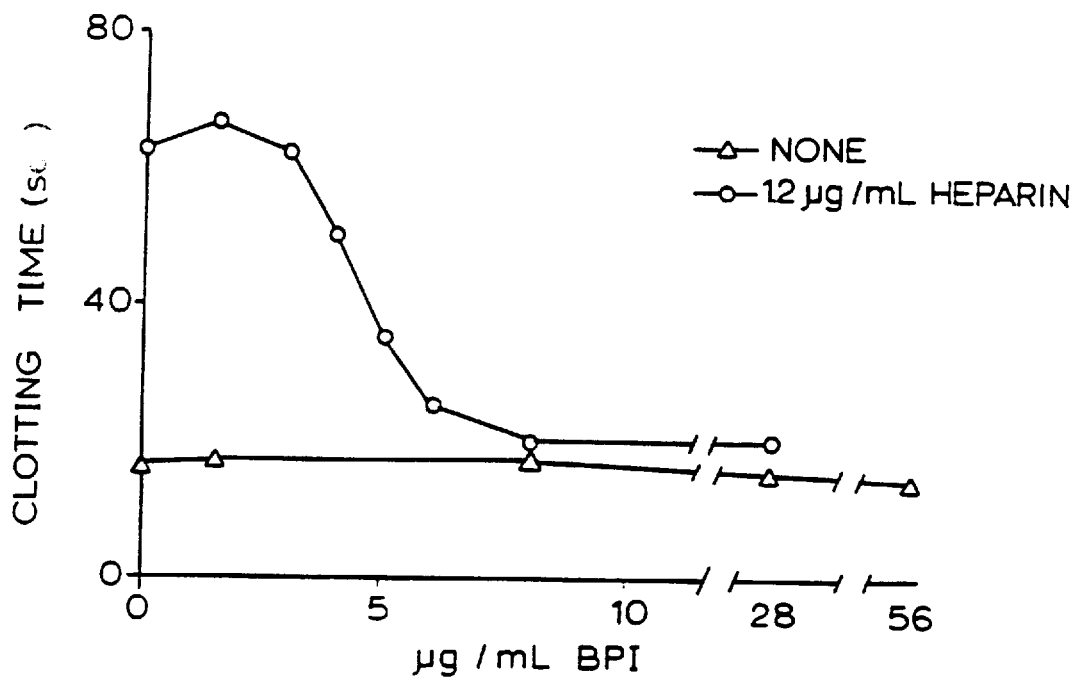
FIG. 5 depicts a graph showing the effect of rBPI$_{23}$ on heparin-mediated lengthening of thrombin time in human plasma.

The effect of BPI protein products on heparin-mediated lengthening of thrombin time, i.e., the time required for clotting of a mixture of thrombin and plasma was examined. Thrombin time is lengthened by the presence of endogenous or exogenous inhibitors of thrombin formation, such as therapeutically administered heparin. Agents which neutralize the anti-coagulant effects of heparin will reduce the thrombin time measured by the test. Human citrated plasma (200 μL) was incubated for 1 minute at 37° C. with either 15 μL of diluent (0.15M NaCl, 0.1M Tris, pH 7.4) or 15 μL of the diluent also containing 25 μg/mL heparin (187 units/mg). Various concentrations of rBPI$_{23}$ (from 0.0 to 56 μg/mL) in a volume of 15 μL were added, followed immediately by 100 μL of thrombin reagent (Sigma Chemical Co., No. 845-4). Clotting time (thrombin time) was measured using a BBL Fibrometer (Becton Dickinson Microbiology Systems, Cockeysville, Md.). The results shown in FIG. 5 establish that rBPI$_{23}$ inhibits the heparin-mediated lengthening of thrombin time. In the absence of heparin, rBPI$_{23}$ had no effect on the assay even at concentrations as high as 56 μg/mL.

EXAMPLE 6

HEPARIN NEUTRALIZATION BY BPI PROTEIN PRODUCTS: EFFECT OF BPI ON PARTIAL THROMBOPLASTIN TIME

Figure 6:
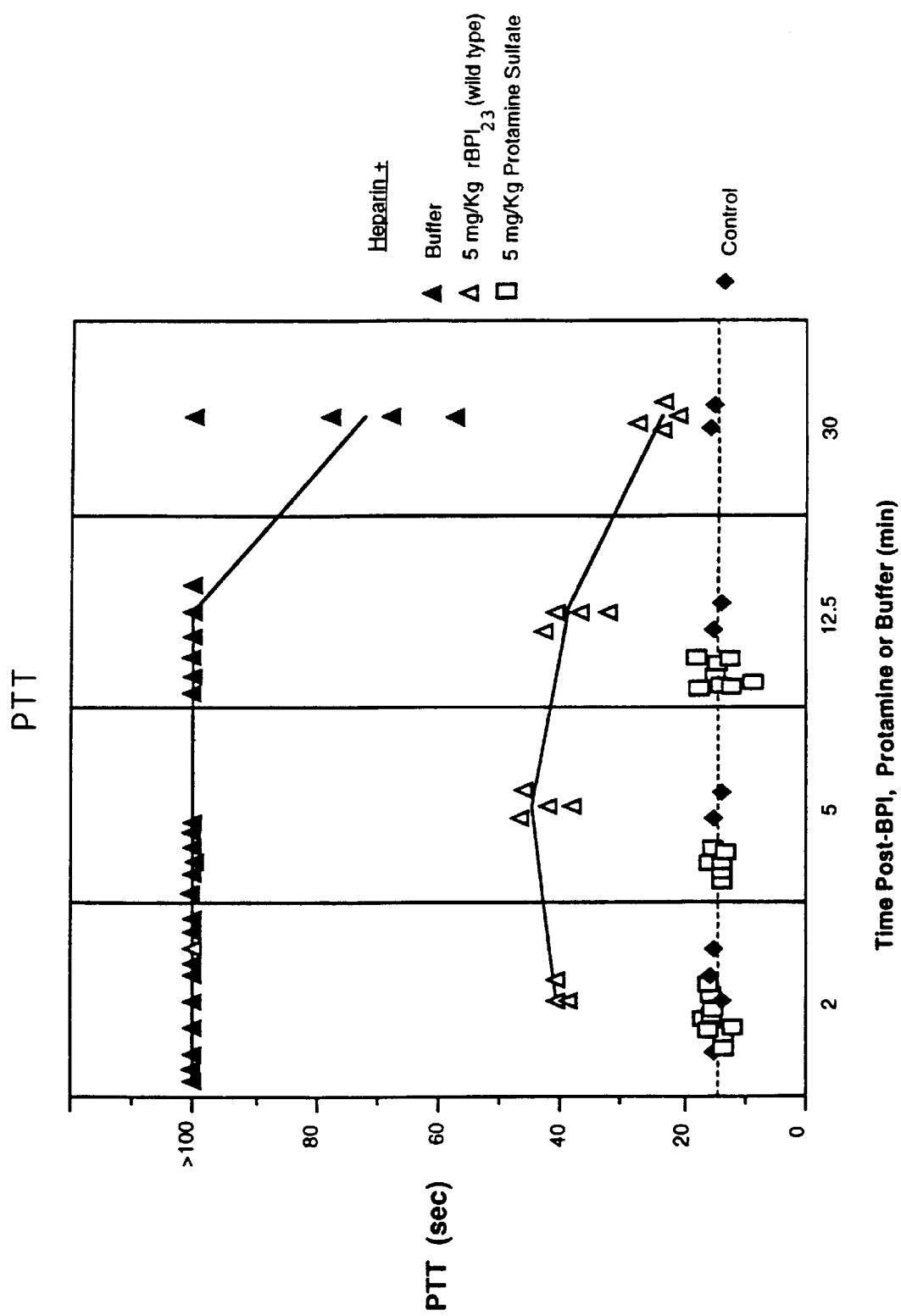
FIG. 6 depicts a graph showing the effect of rBPI$_{23}$ on partial thromboplastin time.

The effect of rBPI$_{23}$, or protamine sulfate on partial thromboplastin time (PTT) in heparinized rats was determined. PTT is lengthened by the presence of endogenous or exogenous inhibitors of thrombin formation, such as therapeutically administered heparin. Agents which neutralize the anti-coagulant effects of heparin will reduce the PTT as measured by the test. Sprague-Dawley rats housed under NIH guidelines were administered with 100 U/kg heparin by bolus intravenous injections via the animals' tail vein followed by administration of 5 mg/kg rBPI$_{23}$, 5 mg/kg protamine sulfate or buffer. The PTT was then determined from blood samples collected from the abdominal aorta of the previously anesthetized animals. The PTT of untreated animals was also determined. The results shown in FIG. 6 establish that both rBPI$_{23}$ and protamine had an immediate effect on the PTT of the treated animals. These animal data confirm the heparin neutralizing effects of BPI protein products as shown in Examples 2–5.

The collective results from Examples 1 through 6 show that rBPI$_{23}$ binds to heparin in direct binding assays and effectively neutralizes heparin inhibition of coagulation proteases. Based on these characteristics, BPI protein products are projected to be useful in the clinical neutralization of heparin anti-coagulant effects in dosages generally corresponding functionally to those recommended for protamine sulfate, but are not expected to possess the severe hypotensive and anaphylactoid effects of that material.

EXAMPLE 7

THERAPEUTIC EFFECTS OF BPI PROTEIN PRODUCTS FOR CHRONIC INFLAMMATORY DISEASE: COLLAGEN INDUCED ARTHRITIS MODEL

A further aspect of the present invention relates to the discovery of the utility of BPI to treat and prevent the effects of chronic inflammatory disease states such as arthritis, including rheumatoid and reactive arthritis, psoriasis, inflammatory bowel disease, Crohn's disease, ulcerative colitis, lupus erythematosus, autoimmune uveitis, Lyme disease, and asthma. Exemplary methods are provided for treating subjects suffering from arthritis comprising administering an effective amount of a BPI protein product in order to prevent or treat arthritis. The BPI protein product may be administered topically, or by injection such as intraarticularly, intravenously, intramuscularly or subcutaneously or by other parenteral and non-parenteral methods.

The effect of administration of BPI protein products was studied in a collagen-induced arthritis model. Specifically, arthritis was induced in mice by intradermal immunization of bovine Type II collagen at the base of the tail according to the method of Stuart et al., *J. Clin. Invest.*, 69:673–683 (1982). Generally, mice begin to develop arthritic symptoms at Day 21 after collagen immunization. The arthritic scores of the treated mice were then evaluated in a blinded fashion over a period of 120 days for mice treated on each of days 21–25 with doses of either rBPI$_{23}$, thaumatin control protein, or buffer which were injected intravenously via the tail vein.

Specifically, bovine Type II collagen (Southern Biotechnology Associates, Inc., Birmingham Ala.) was administered via intradermal injection (0.1 mg/mouse) at the base of the tail on day 0 to groups of ten male mice (Mouse/DBA/1J), each weighing approximately 20–25 g. rBPI$_{23}$ was dissolved in 0.5M NaCl, 20 mM sodium acetate, pH 6.0 and diluted with PBS buffer (1 mg/ml) for administration at 0.125 mg/mouse. Thaumatin protein in PBS (0.121 mg/mouse) or PBS buffer alone (0.1 ml) were administered as controls.

Figure 7:
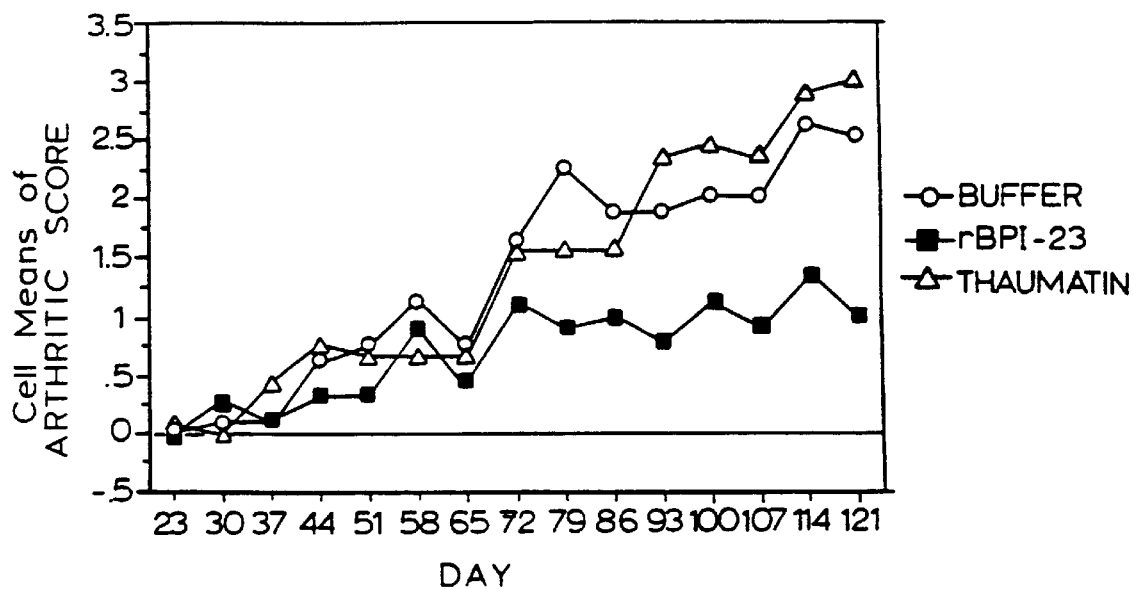
FIG. 7 depicts a graph showing the effect of rBPI$_{23}$ and thaumatin control protein on arthritic scores in a collagen-induced arthritis model with mild arthritis.

The results shown in FIG. 7 demonstrate that the rBPI$_{23}$ has a statistically significant effect in reducing the arthritic score of treated mice compared with the PBS buffer and thaumatin protein controls.

EXAMPLE 8

THERAPEUTIC EFFECTS OF BPI PROTEIN PRODUCTS IN COMPARISON WITH PROTAMINE SULFATE FOR CHRONIC INFLAMMATORY DISEASE: COLLAGEN INDUCED ARTHRITIS MODEL

Figure 8:
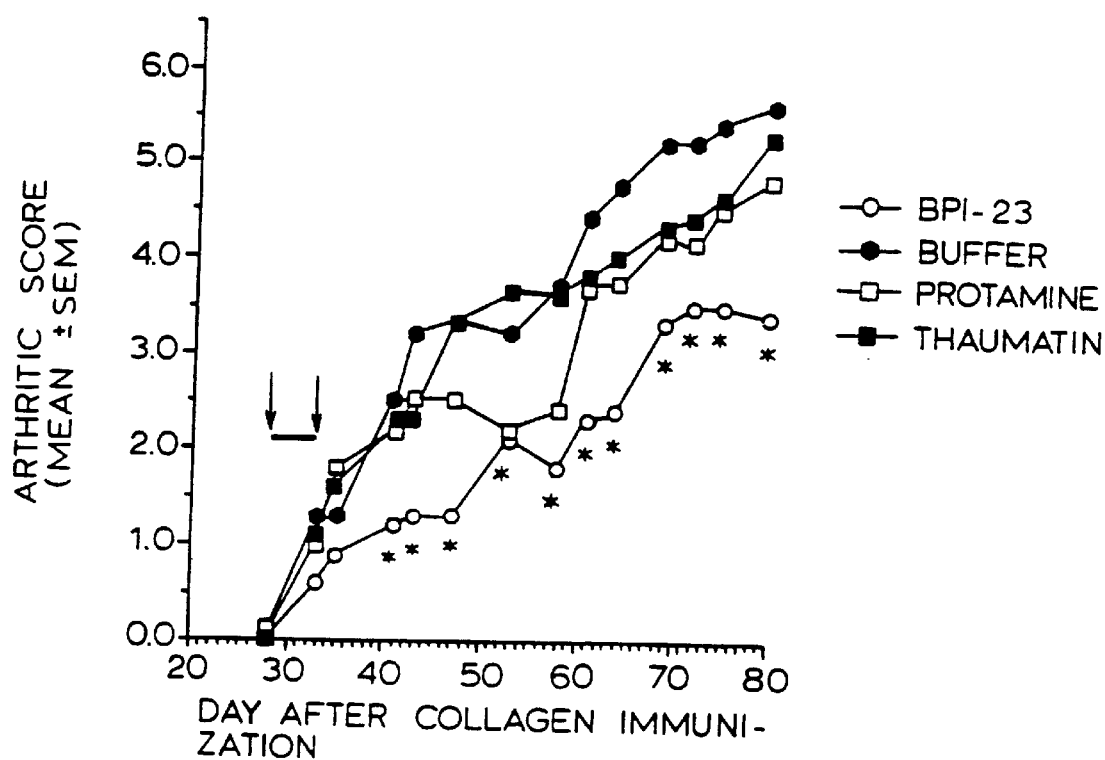
FIG. 8 depicts a graph showing the effect of rBPI$_{23}$ and protamine on arthritic scores in a collagen-induced arthritis model with severe arthritis.

The collagen-induced arthritis model of Example 7 was used to evaluate the performance of a BPI protein product in comparison with protamine sulfate, using both thaumatin protein and buffer as controls. Specifically, rBPI$_{23}$ was dissolved in 0.5M NaCl, 20 mM sodium acetate, pH 6.0 and diluted with PBS buffer (1 mg/ml) and was administered at 0.125 mg/mouse. The other test materials were administered at the following dosages: protamine sulfate (Sigma Chemical Co) (0.13 mg/mouse), thaumatin (0.121 mg/mouse), and PBS buffer (0.1 ml). Each of four groups of ten mice received test or control materials through intravenous injection via the tail vein on each of days 28 through 32. FIG. 8 discloses the results of arthritic scores for the various treatment and control protocols evaluated at days 28–80. The stars (*) in FIG. 8 represent a statistically significant difference between rBPI$_{23}$ and buffer at p<0.01 while the pluses (+) represent a statistically significant difference between rBPI$_{23}$ and buffer at p<0.05. These results show that the rBPI$_{23}$ significantly reduced arthritic score for mice treated in the model system.

EXAMPLE 9

GRAM-NEGATIVE INDUCED REACTIVE ARTHRITIS MODELS

Figure 9:
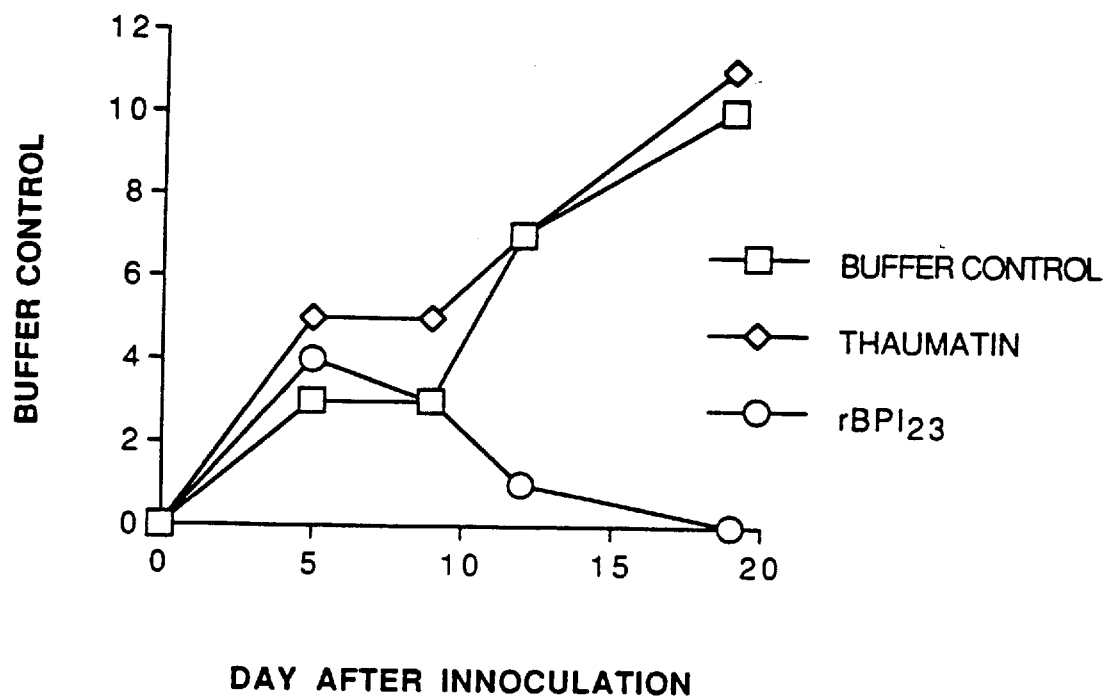
FIG. 9 depicts a graph showing the effect of rBPI$_{23}$ on the incidence of arthritis in a Yersinia-induced arthritis model.

The effect of administration of BPI protein products to treat reactive arthritis was studied in a *Yersinia enterocolitica* reactive arthritis model according to the method of Yong et al., *Microbial Pathogenesis,* 4:305–310 (1988). Specifically, BPI protein products are administered to DBA/2J male mice which had previously been injected intravenously through the tail vein with *Yersinia enterocolitica cWA* 0:8 T2 (i.e., lacking the virulence plasmid according to Yong et al. supra) at a dosage of 4×10$^8$ bacteria calculated to induce a non-septic arthritis in the mice. Each of three groups of 15 mice each received test or control materials through intravenous injection via the tail vein. The mice were given either rBPI$_{23}$ at a dosage of about 5.0 mg/kg dissolved in a buffer of 20 mM sodium citrate, 150 mM sodium chloride, 0.1% poloxamer 188, 0.002% polysorbate 80, pH 5.0; thaumatin protein at a dosage of about 5.0 mg/kg dissolved in the buffer of 20 mM sodium citrate, 150 mM sodium chloride, 0.1% poloxamer 188, 0.002% polysorbate 80, pH 5.0; or the buffer alone. The results depicted in FIG. 9 show that the BPI protein product significantly reduced the incidence of reactive arthritis versus the buffer or thaumatin control protein.

Figure 10:
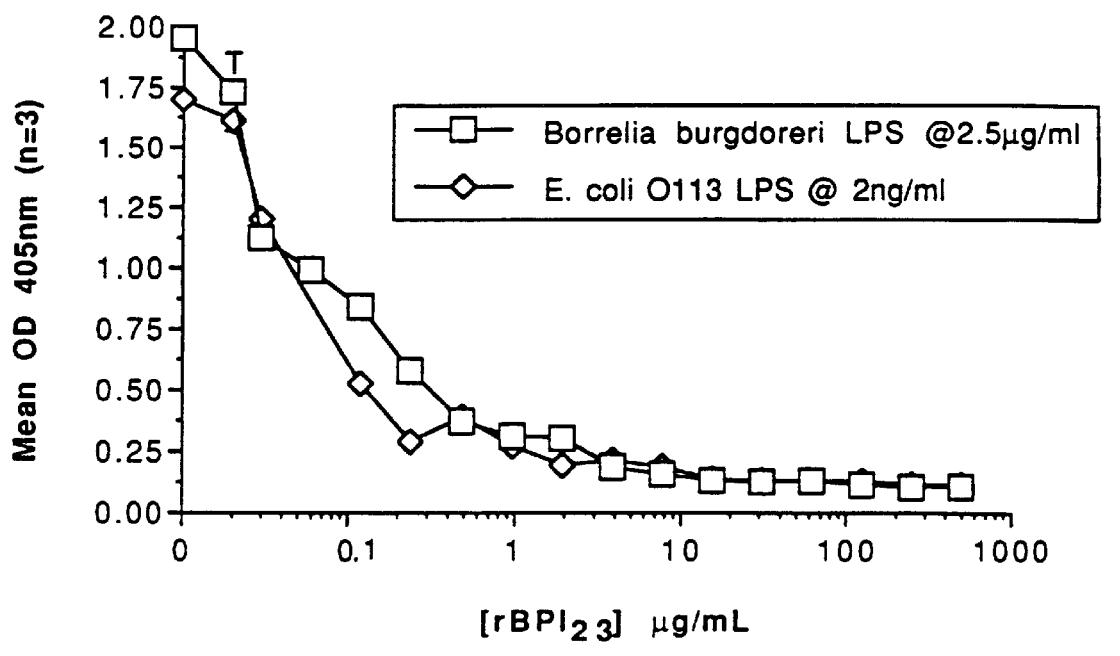

*Borrelia burgdorferi* is the pathogen responsible for Lyme Disease and associated arthritis and it possesses an LPS-like complex on its cell walls which is different from but structurally related to that of *E. coli.* The effect of administration of BPI protein products on inhibition of *Borrelia burgdorferi* LPS in a Limulus Amoebocyte Lysate (LAL) inhibition assay was determined. Specifically, an LAL assay according to the method of Example 15 was conducted measuring the effect of rBPI$_{23}$ on *Borrelia burgdorferi* LPS administered at 2.5μg/mL and *E. coli* 0113 LPS administered at 2 ng/mL. The results depicted in FIG. 10 show that rBPI$_{23}$ neutralizes the effects of both *Borrelia burgdoriferi* LPS and *E. coli* 0113 LPS in the LAL assay.

EXAMPLE 10

EFFECT OF BPI IN A MOUSE MALIGNANT MELANOMA MODEL

According to this example, a BPI protein product, protamine, and both thaumatin protein and buffer controls were tested for efficacy in a mouse malignant melanoma metastasis model. Specifically, four groups of nine C57BL/6J mice were inoculated with 10$^5$ B16.F10 malignant melanoma cells via intravenous injection into the tail vein on day 0. Either rBPI$_{23}$ (0.13 mg/mouse), protamine sulfate (0.13 mg/mouse), thaumatin (0.13 mg/mouse) or PBS buffer (0.1 ml/mouse) were intravenously administered into the tail vein of the mice on days 1, 3, 6, 8, 10, 13, 15, 17, and 19. The animals were sacrificed via cervical dislocation on Day 20 for observation of lung tissues. The lobes of each lung were perfused and inflated by injecting 3 ml water into the lung via the trachea. Superficial tumor nodules were then counted with the aid of a dissecting microscope and the number of tumors found per group analyzed for statistically significant differences. While the data was not statistically significant, animals treated with BPI$_{23}$ had the lowest tumor load, followed by those treated with protamine, the thaumatin protein control and the buffer control. The lack of statistical significance (tumor number did not adequately reflect tumor size) indicated that a more specific assay methodology would be needed to determine the tumor load.

EXAMPLE 11

EFFECT OF BPI IN A MOUSE MALIGNANT MELANOMA MODEL

A BPI protein product, protamine, and both thaumatin protein and buffer controls were again tested for efficacy in the mouse malignant melanoma metastasis model of Example 10. Specifically, six groups of C57BL/6J mice were inoculated with 10$^5$ B16.F10 malignant melanoma cells via intravenous injection into the tail vein on day 0. Either rBPI$_{23}$ (0.125 mg/mouse), protamine sulfate (0.125 mg/mouse), thaumatin (0.125 mg/mouse) or PBS buffer as set out in Table 2 below were intravenously administered into the tail vein of the mice on days 1, 2, 5, 7, 9, 12, 14, 16, and 19. All animals in groups A-D were sacrificed by cervical dislocation on day 20 for observation of lung tissues. The lungs were removed and placed into a beaker of cold water. The lobes of each lung were then perfused and inflated by injecting 3 ml of water into the lung via the trachea. Superficial tumor nodules are then analyzed for melanin content.

TABLE 2

| Group | Control/Test Article | No. of Animals |
| --- | --- | --- |
| A | Buffer | 10 |
| B | Protamine | 10 |
| C | Thaumatin | 10 |
| D | rBPI$_{23}$ | 10 |
| E | Buffer | 5 |
| F | rBPI$_{23}$ | 5 |

Figure 11:
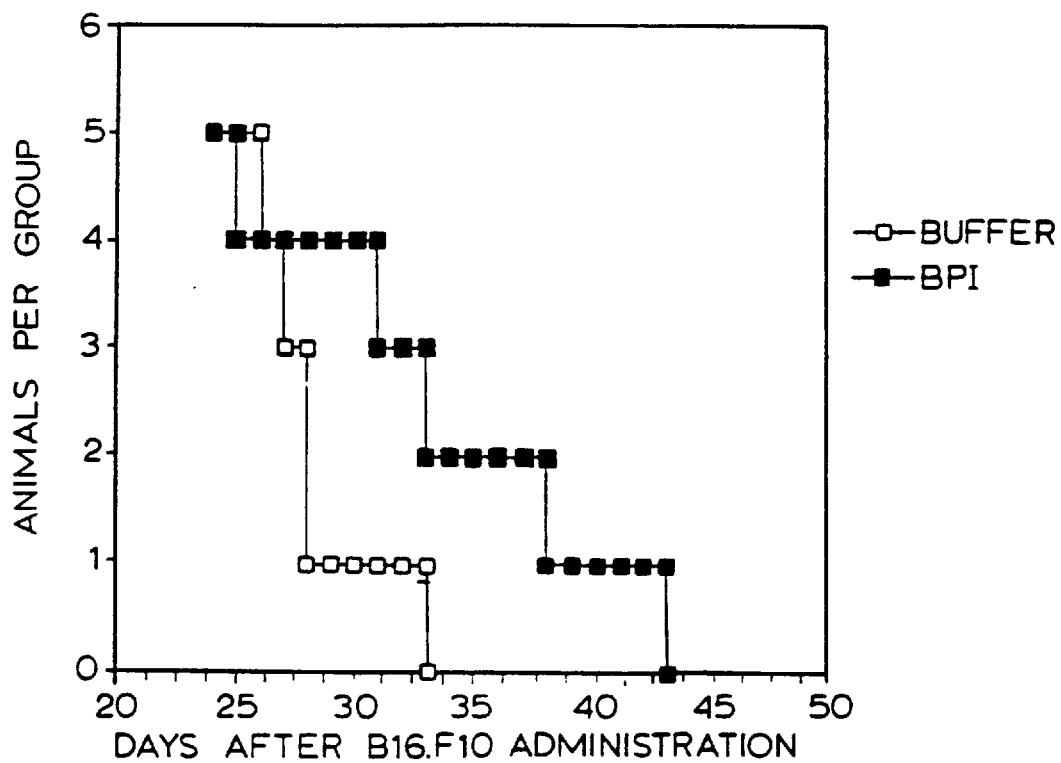
FIG. 11 depicts a graph showing survival of mice treated with BPI or a buffer in a mouse melanoma metastasis model.

Groups E and F comprising animals treated with either buffer or rBPI$_{23}$ respectively were not sacrificed but were observed once daily for mortality. FIG. 11 shows the survival data for the two groups of animals. Although all ten of the animals had died by day 43, the BPI treated mice generally survived significantly longer than the untreated mice indicating that BPI had an anti-angiogenic effect and slowed metastasis of the melanoma tumors.

Given the above, according to an additional aspect of the invention, BPI protein products may be used to inhibit Kaposi's Sarcoma in a model system such as that of Miles et al., VII International Conference on AIDS, Florence, Italy, Paper 41(8), 1991.

EXAMPLE 12

EFFECT OF BPI ON ENDOTHELIAL CELL PROLIFERATION

Murine cerebral capillary endothelial cells (EC) as described in Bauer, *Microvascular Research* 37: 148–161

(1989) were passaged in Medium 199 containing Earle's salts, L-glutamine and 2.2 g/l of sodium bicarbonate (Gibco, Grand Island, N.Y., #400-100EB), plus 10% heat inactivated fetal calf serum (Irvine Scientific, Irvine, Calif.) and 1% penicillin/streptomycin (Gibco, #600-5140AG). Harvesting of the confluent cells was performed by trypsinization with trypsin-EDTA (Gibco #610-5300PG) for 3 minutes. The trypsinization was stopped by adding 10 ml of the passage medium to the flask. Proliferation assays were performed on freshly harvested EC in standard flat bottom 96 well microtiter plates. A final volume of 200 µl/well was maintained for each well of the assay. A total of $4 \times 10^4$ EC were added to each well with varying concentrations of $rBPI_{23}$, thaumatin control protein or buffer control. After 48 hours of culture in a 5% $CO_2$ incubator, 1 µCi of [methyl-$^3$H] thymidine in 10 µl of Medium 199 was added to each well. After a 24 hour pulse, the EC cells were harvested by trypsinization onto glass microfiber filters and incorporated [$^3$H]thymidine was quantitated with a gas proportional solid phase beta counter.

Figure 12:
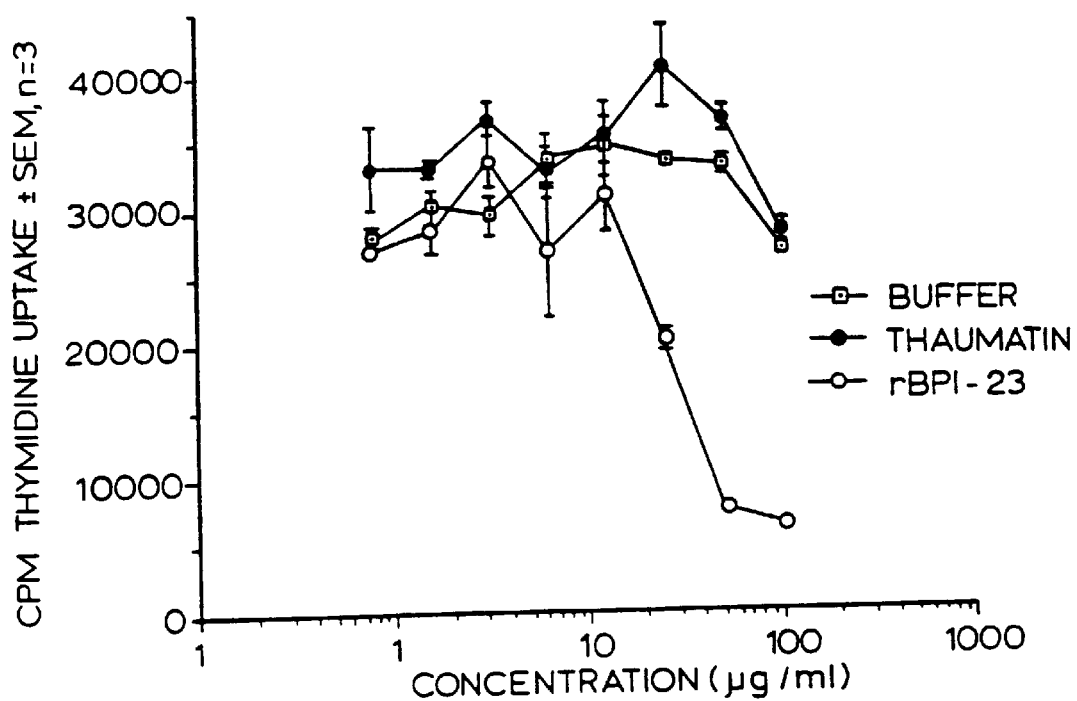
FIG. 12 depicts a graph showing the effect of rBPI$_{23}$ on Type II murine capillary endothelial cell proliferation.

Concentration dependent inhibition of EC cell proliferation by $rBPI_{23}$ is shown in FIG. 12. No effect was observed when similar concentrations of thaumatin or equal volumes of the buffer were added to the wells. The first inhibition of proliferation is observed at 12.4 µg/ml $rBPI_{23}$ and the effect appears to be maximal at 50 µg/ml. The growth of the EC cells is known to be dependent on FGF-2 (bFGF) in the calf serum and FGF-2 requires cell surface heparan for receptor activation (Yayon et al., *Cell* 64:841–848, 1991). Without intending to be bound by a theory of the invention, it is believed that $rBPI_{23}$ bound to cell surface heparan on the EC cells interferes with the activation of the cells by FGF-2.

Direct binding studies of $rBPI_{23}$ on the EC cells were performed by harvesting the 10x passaged cells from a confluent flask and resuspending the trypsinized cells in 12.5 ml of culture medium. 0.5 ml of the suspension was added to each well of a standard 24 well tissue culture plate and incubated overnight. The plate was washed with 0.1% bovine serum albumin in phosphate buffered saline containing calcium and magnesium. (Gibco.) After washing, 0.5 ml of the BSA/PBS was added per well. Preliminary experiments indicated that 50 ng/ml of $^{125}$I-labeled $rBPI_{23}$ added to the wells produced approximately 30,000 specific cpm after a 3 hour, 4° C. incubation with 3x washing in PBS and lysis with 1M NaOH from gamma counting of the lysate.

Figure 13:
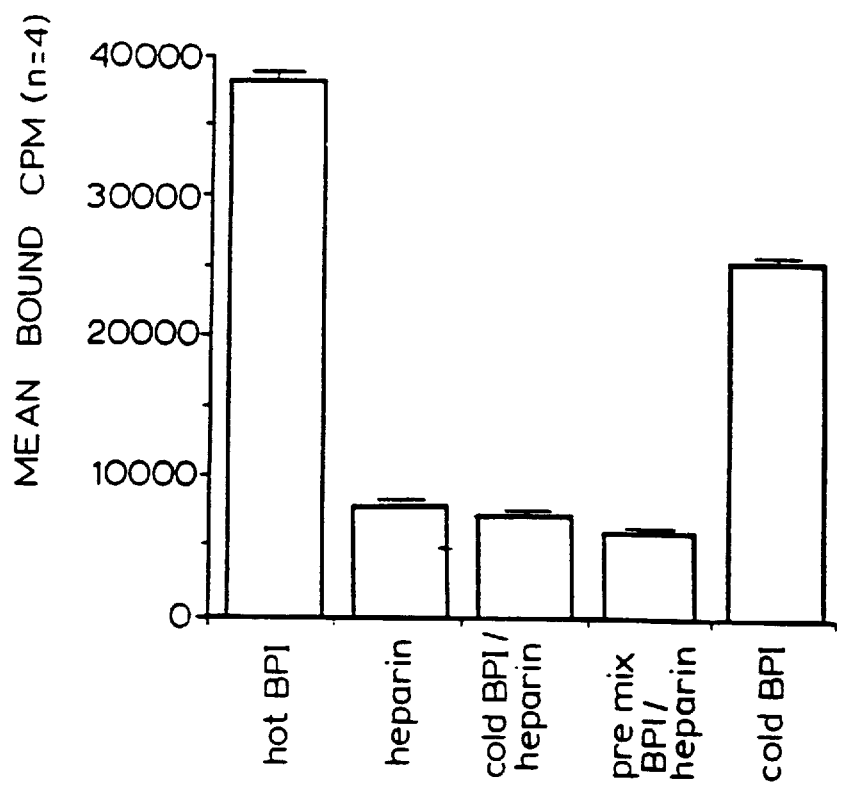
FIG. 13 illustrates BPI binding to epithelial cells.

The specific binding of 50 ng/ml $^{125}$I-labeled, "hot" $rBPI_{23}$ to the EC cells could be competed by addition of 20 µg/ml heparin (Sigma, Grade I). Similar competition was observed for unlabeled ("cold") $rBPI_{23}$ added to the binding culture. The combination of unlabeled $rBPI_{23}$ with heparin (concurrently added or pre-mixed prior to addition) could not reduce the binding below the heparin only competition (FIG. 13). These data indicate that $rBPI_{23}$ binds to endothelial cells via heparin-like molecule and that this binding appears to interfere with EC cell proliferation to a heparin binding growth factor (FGF-2).

EXAMPLE 13

PREPARATION OF 15-MER SYNTHETIC PEPTIDES OF BPI

In order to assess biological properties of peptide fragment BPI protein products, 15-mer amino acid synthetic peptides based on the 23 kD amino terminal fragment of BPI were prepared and evaluated for heparin-binding activity, activity in a Limulus Amoebocyte Lysate Inhibition (LAL) assay and bactericidal activity. Specifically, 47 synthetic peptides each comprising 15 amino acids and overlapping the adjacent peptides by 11 amino acids were prepared, in duplicate, based on the sequence of $rBPI_{23}$ described above.

Peptides were simultaneously synthesized according to the methods of Maeji et al., *ImmunoL Methods*, 134:23–33 (1990) and Gammon et al., *J. Exp. Med.*, 173:609–617 (1991), utilizing the solid-phase technology of Cambridge Research Biochemicals Ltd. under license of Coselco Mimotopes Pty Ltd. Briefly, the sequence of $rBPI_{23}$ (1–199) was divided into 47 different 15-mer peptides that progressed along the linear sequence of $rBPI_{23}$ by initiating a subsequent peptide every fifth amino acid. This peptide synthesis technology allows for the simultaneous small scale synthesis of multiple peptides on separate pins in a 96-well plate format. Thus, 94 individual pins were utilized for this synthesis and the remaining to pins (B,B) were subjected to the same steps as the other pins without the addition of activated FMOC-amino acids. Final cleavage of the 15-mer peptides from the solid-phase pin support employed an aqueous basic buffer (sodium carbonate, pH 8.3). The unique linkage to the pin undergoes a quantitative diketopiperazine cyclization under these conditions resulting in a cleaved peptide with a cyclo(lysylprolyl) moiety on the carboxyl-terminus of each peptide. The amino-termini were not acetylated so that the free amino group could potentially contribute to anion binding reactions. An average of about 15 µg of each 15-mer peptide is recovered per well.

EXAMPLE 14

HEPARIN BINDING BY 15-MER SYNTHETIC PEPTIDES OF BPI

Figure 14:
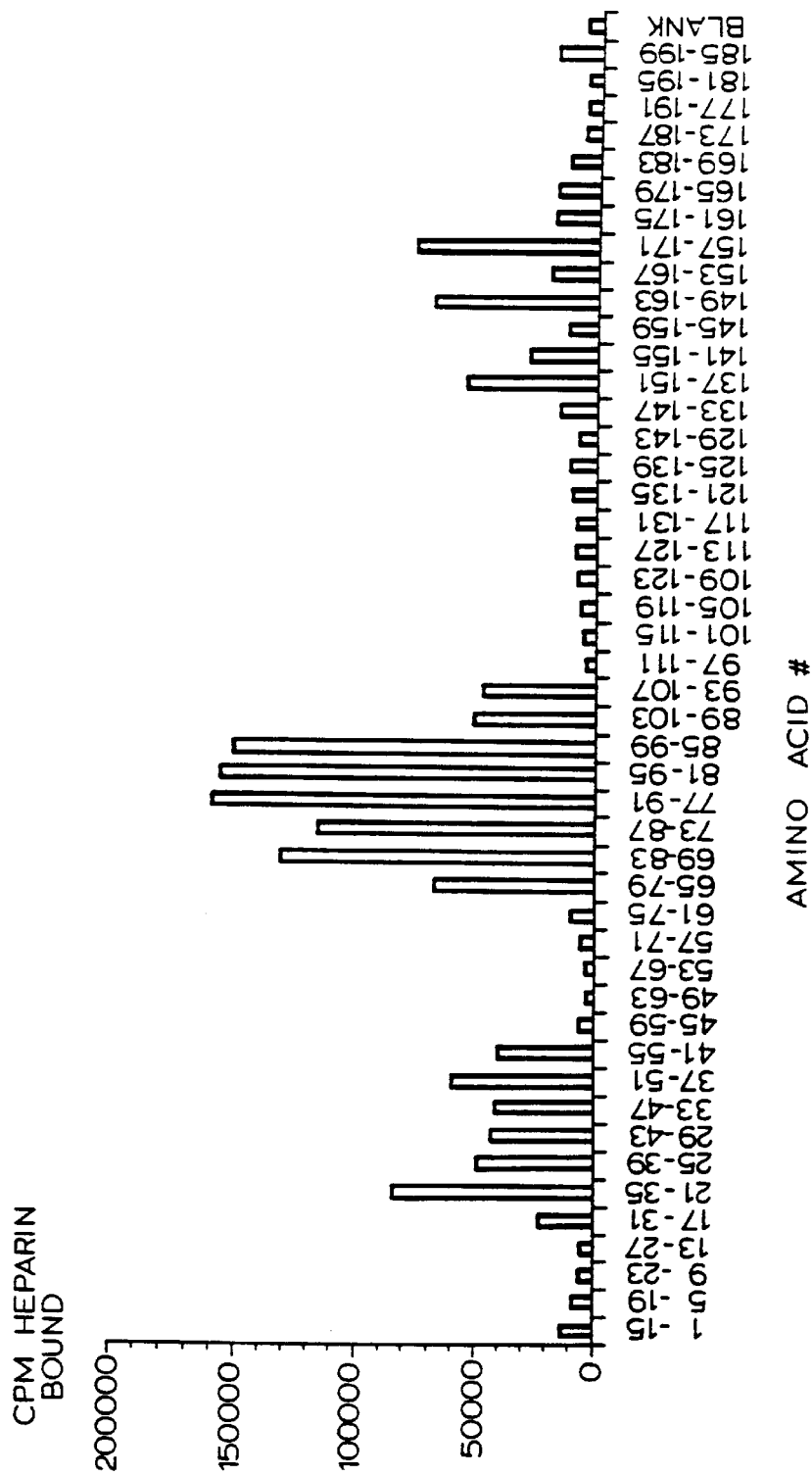
FIG. 14 depicts a graph of a heparin binding assay for synthetic BPI peptides.

The synthetic BPI protein product peptides described above were subjected to a heparin binding assay according to the methods described in Example 1. The results, as shown in FIG. 14, indicate the existence of three separate functional domains with heparin binding activity; the first extending from about amino acids 21–55; the second extending from about amino acids 65–107; and the third extending from about amino acids 137–171. Material from blank control pins had no heparin binding effects.

EXAMPLE 15

EFFECT OF 15-MER SYNTHETIC PEPTIDES OF BPI ON AN LAL ASSAY

The synthetic BPI protein product peptides were subjected to a Limulus Amoebocyte Lysate (LAL) inhibition assay to determine LPS binding properties. Specifically, the synthetic BPI peptides were mixed in Eppendorf tubes with a fixed concentration of *E. coli* 0113 LPS (4 ng/ml final) and incubated at 37° C. for 3 hours with occasional shaking. Addition controls comprising 0.05 µg/mL were also tested. Following incubation, 360 µl D-PBS was added per tube to obtain an LPS concentration of 200 pg/mL for the LAL assay. Each sample was then transferred into IMMULON II strips (Dynatech, Chantilly, Va.) in volumes of 50 µl per well.

Limulus amoebocyte Lysate (Quantitative chromogenic LAL kit, Whitaker Bioproducts, Inc., Walkersville, Md.) was added at 50 µl per well and the wells were incubated at room temperature for 25 minutes. Chromogenic substrate was then added at a volume of 100 µl per well and was well mixed. After incubation for 20 to 30 minutes at room temperature, the reaction was stopped with addition of 100 µl of 25% acetic acid. Optical density at 405 nm was then measured in a multiplate reader (Vmax, Molecular Dynamics, Menlo Park, Calif.) with the results shown in FIG. 15 in terms of percent inhibition of LPS. The data in FIG. 15 indicate at least three major domains with significant LAL inhibition; the first extending from amino acids 17–55; the second extending from about amino acids 73–99 and the third extending from about amino acids 137–163. Other individual peptides also exhibit LAL inhibition. In contrast, material from blank control pins did not exhibit LPS neutralizing effects as measured by the LAL assay.

EXAMPLE 16

BACTERICIDAL EFFECTS OF 15-MER SYNTHETIC PEPTIDES OF BPI

The synthetic BPI protein product peptides were tested for bactericidal effects against the rough mutant *E. coli* J5 bacteria in a radial diffusion assay. Specifically, an overnight culture of *E. coli* J5 was diluted 1:50 into fresh tryptic soy broth and incubated for 3 hours at 37° C. to attain log phase. Bacteria were then pelleted at 3,000 rpm for 5 minutes in a Sorvall RT6000B. 5mL of 10 mM sodium phosphate buffer (pH 7.4) was added and the preparation was re-centrifuged. The supernatant was decanted and 5 mL of fresh buffer was added, the bacteria were resuspended and their concentration was determined by measurement of absorbance at 590 nm. Absorbance of $1.25 \times 10^9$ CFU/mL suspension equals 1.00. The bacteria were diluted to $4 \times 10^6$ CFU/mL in 10 mL of molten underlayer agarose (approximately 45° C.) and inverted repeatedly to mix with 15 mL polypropylene tubes used for this purpose.

The entire contents of the tube were poured into a perfectly level square petri dish and distributed evenly by rocking the dish side to side. The agarose hardened in less than 30 seconds and had a uniform thickness of about 1 mm. A series of wells were then punched into the hardened agarose using a sterile 3 mm punch attached to a vacuum apparatus. The punch was sterilized with 100% alcohol and allowed to air dry.

10 $\mu$L of the synthetic BPI peptides were carefully pipetted into each well. As controls, pH 8.3 buffer was added to a separate well (as positive controls, 5 $\mu$g/mL and 1 $\mu$g/mL concentration of rBPI$_{23}$ was also added. In addition, products from the blank pins B and B were tested as controls. The plate was allowed to incubate at 37° C. for 3 hours and 10 mL of molten overlayer agarose (at approximately 45° C.) was then added into the level petri dish, allowed to harden and incubated overnight at 37° C. A clear zone was seen against the lawn of bacteria in those wells having bactericidal activity. In order to visually enhance this zone, a dilute Coomassie solution (0.002% Coomassie Brilliant Blue, 27% methanol, 15% formaldehyde (37% stock solution) and H$_2$O) was poured over the agar and allowed to stain for 24 hours. The bacterial zones were measured with a Mitutoyo micrometer.

Figure 16:
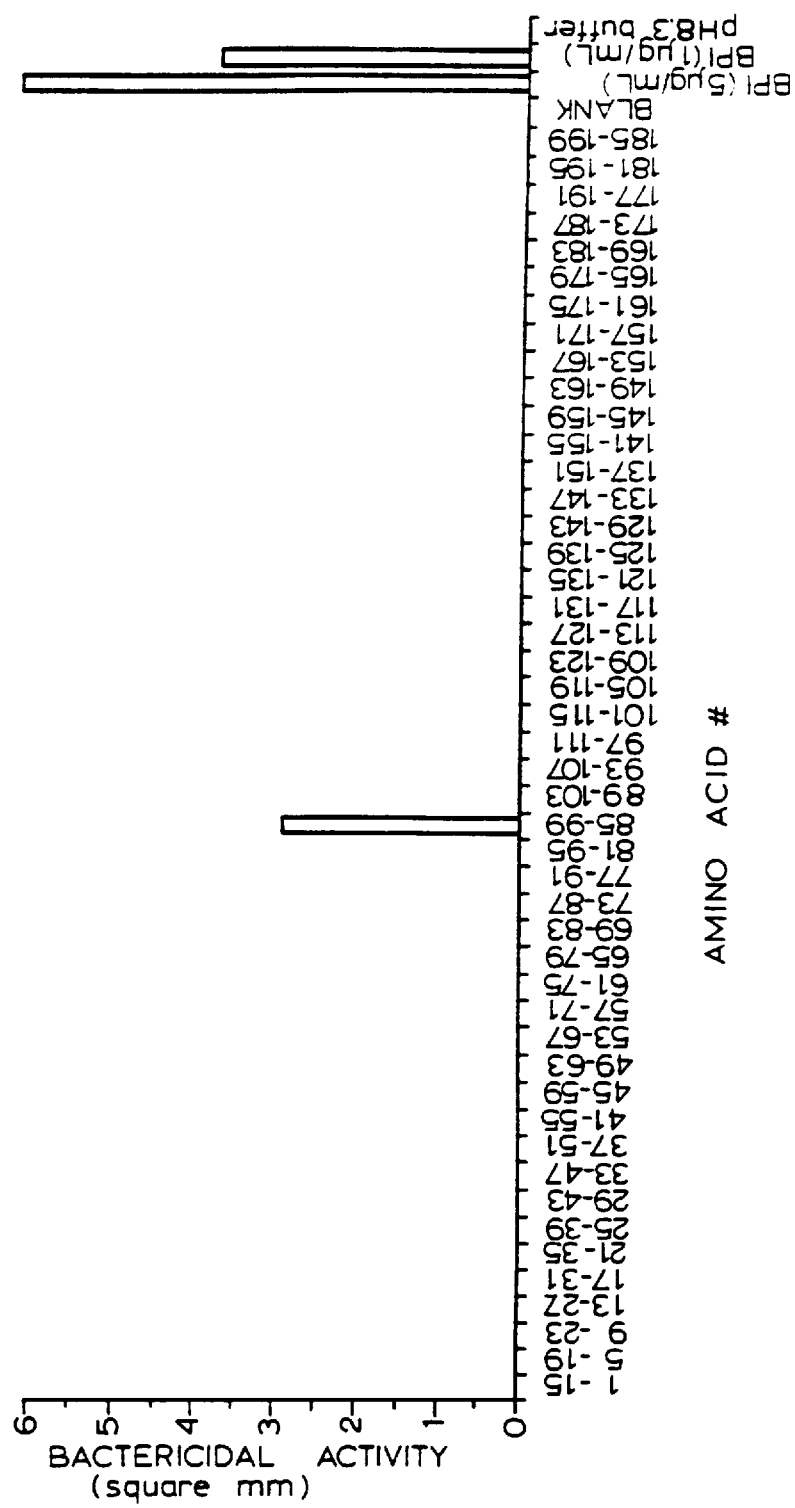
FIG. 16 depicts a graph of a radial diffusion bactericidal assay for synthetic BPI peptides (with amino numbering according to SEQ ID NO: 2)

The results of the assay are shown in FIG. 16 where the only synthetic BPI peptide seen to have bactericidal activity was a fragment corresponding to amino acids 85–99. The positive rBPI$_{23}$ controls also had bactericidal effects while the buffer and blank pin controls did not.

EXAMPLE 17

PREPARATION OF BPI PEPTIDE FRAGMENTS

Based on the results of testing of overlapping peptides in Examples 13 through 16, BPI protein product peptide fragments were prepared by solid phase peptide synthesis according to the methods of Merrifield, *J. Am. Chem. Soc.* 85: 2149 (1963) and Merrifield et al., *Anal. Chem.* 38: 1905–1914 (1966) using an Applied Biosystems, Inc. Model 432 synthesizer. Nine BPI protein product peptides designated BPI-2 through BPI-10 were prepared having the amino acid sequences of portions of amino acid residues 1–199 of rBPI$_{23}$ (SEQ ID NO: 2) as set out in Table 3 below. In the cases of BPI-7, BPI-9 and BPI-10 the peptides represented partial or even multiple repeats of sequence. Specifically, BPI-7 comprises a 20-mer consisting of amino acid residues 90–99 repeated twice in a single linear chain. BPI-10 comprises a 30-mer consisting of amino acid residues 90–99 repeated three times in a single linear chain. BPI-9 comprises a 16-mer comprising amino acid residues 94–99 followed by residues 90–99 in a single linear chain.

TABLE 3

| | BPI Protein Product Peptides | | |
|---|---|---|---|
| Polypeptide No. | Amino Acid Region | Amino Acid Residues | MW (daltons) |
| BPI-2 | 85–99 | 15 | 1828.16 |
| BPI-3 | 73–99 | 27 | 3072.77 |
| BPI-4 | 25–46 | 22 | 2696.51 |
| BPI-5 | 142–163 | 22 | 2621.52 |
| BPI-6 | 112–127 | 16 | 1569.82 |
| BPI-7 | 90–99, 90–99 | 20 | 2644.66 |
| BPI-8 | 90–99 | 10 | 1316.8 |
| BPI-9 | 94–99, 90–99 | 16 | 2131.34 |
| BPI-10 | 90–99, 90–99, 90,99 | 30 | 3958.45 |

EXAMPLE 18

HEPARIN BINDING BY BPI PROTEIN PRODUCT PEPTIDES

Figure 17:
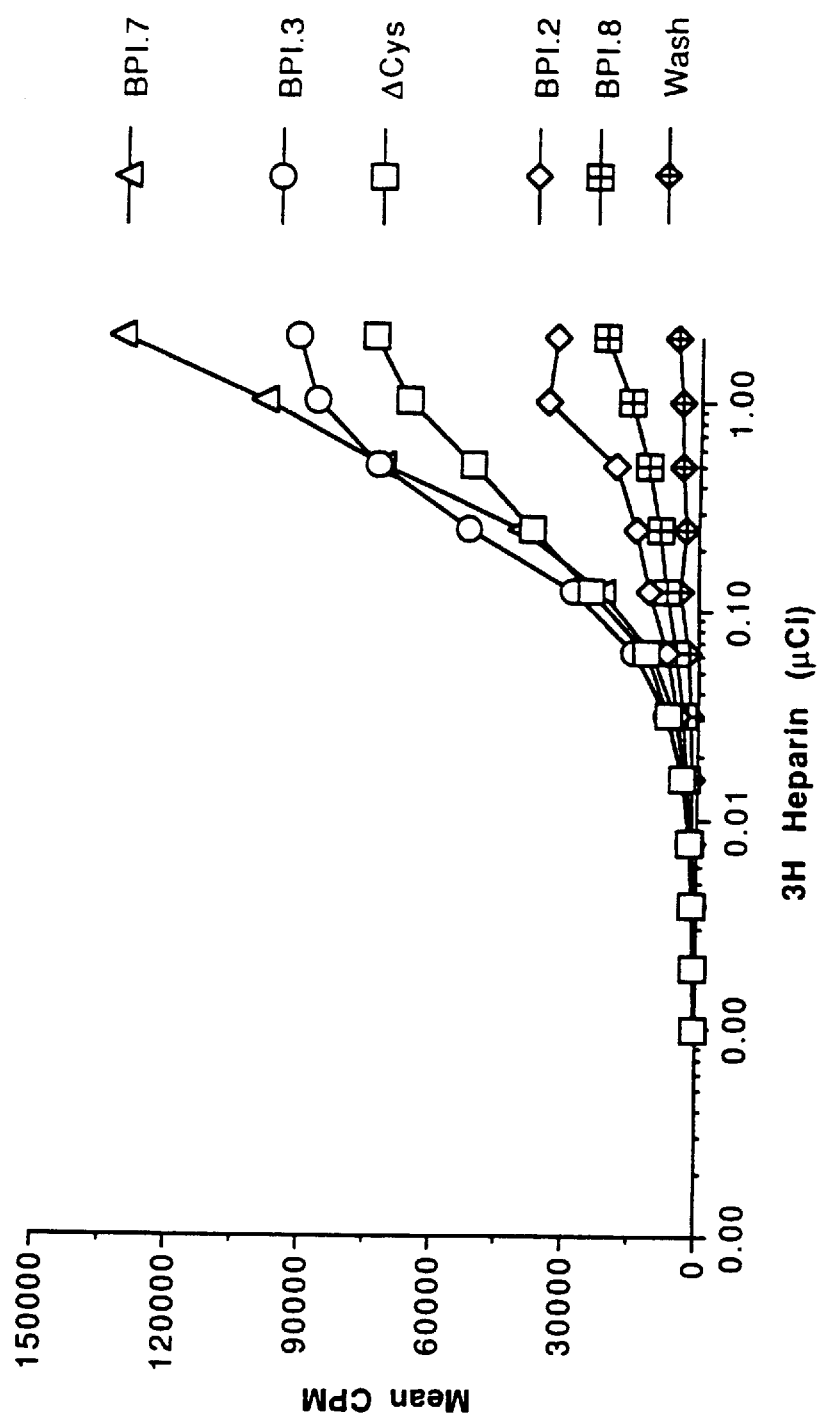
FIG. 17 depicts a graph showing the effect of synthetic BPI peptides in a heparin binding assay.

In this example BPI protein product peptides BPI-2, BPI-3, BPI-4, BPI-6, BPI-7, and BPI-8 along with BPI cys were subjected to a heparin binding assay according to the methods described in Example 1. The results, as shown in FIG. 17 indicate that BPI-7, and BPI-8 have extremely high heparin binding capacity while BPI-2 and BPI-3 have more moderate heparin binding capacity and BPI-4 and BPI-6 have little or no heparin binding capacity.

EXAMPLE 19

HEPARIN NEUTRALIZATION BY BPI PROTEIN PRODUCT PEPTIDES

Figure 18A:
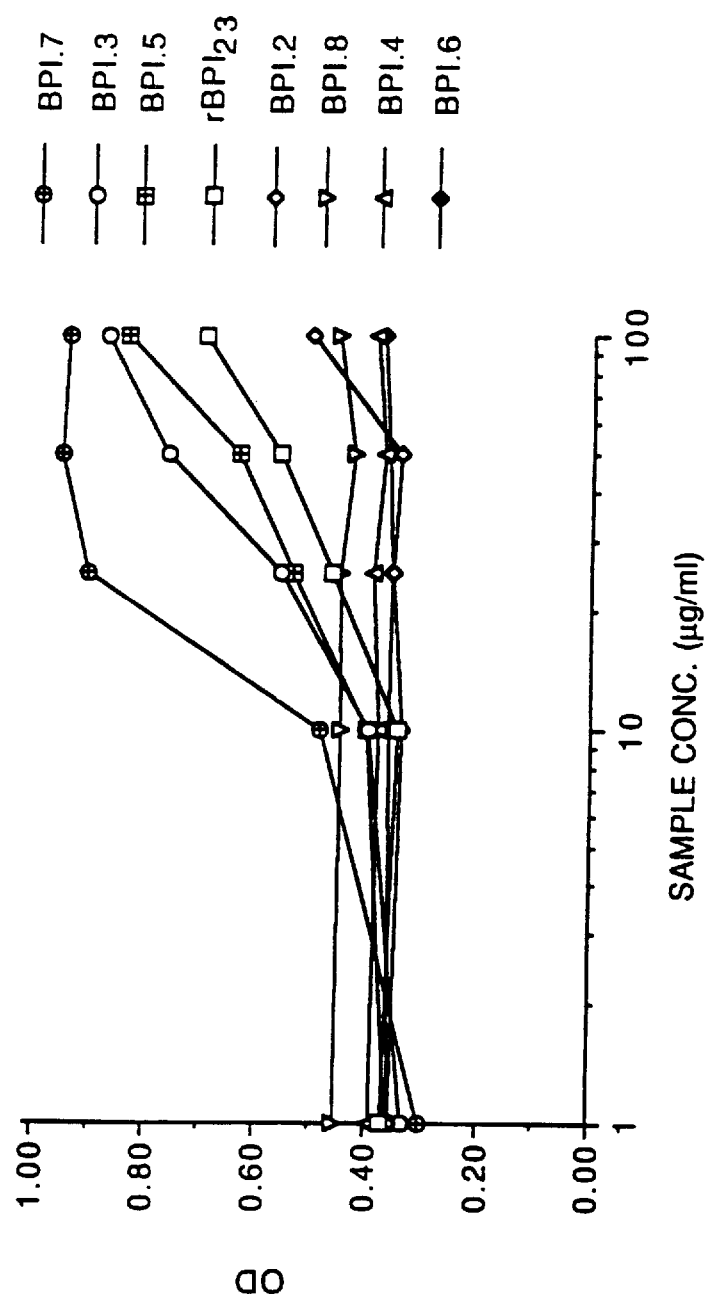
FIGS. 18a and 18b depict graphs showing the effect of synthetic BPI peptides on ATIII/heparin inhibition of thrombin.
Figure 18B:
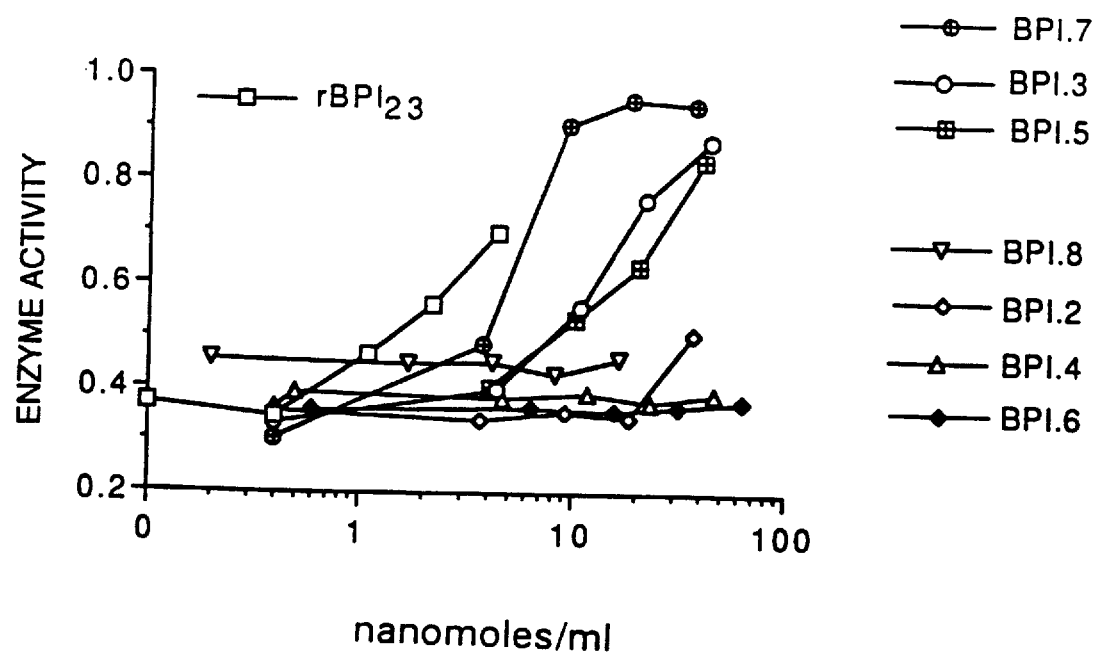

In this example BPI protein product peptides BPI-2, BPI-3, BPI-4, BPI-5, BPI-6, BPI-7, and BPI-8 along with rBPI$_{23}$ were subjected to an assay to determine their effect on thrombin inactivation by ATIII/heparin complexes according to the method of Example 3. Varying concentrations of the BPI protein products ranging from 1.0 $\mu$g/mL to 100 $\mu$g/mL were administered to determine their effect. BPI protein peptides BPI-7, BPI-3, and BPI-5 each had the most significant heparin neutralization effects as shown in FIGS. 18a and 18b which depict the sample concentrations as weight or molar concentrations respectively.

EXAMPLE 20

EFFECT OF BPI PROTEIN PRODUCT PEPTIDES ON AN LAL ASSAY

Figure 19A:
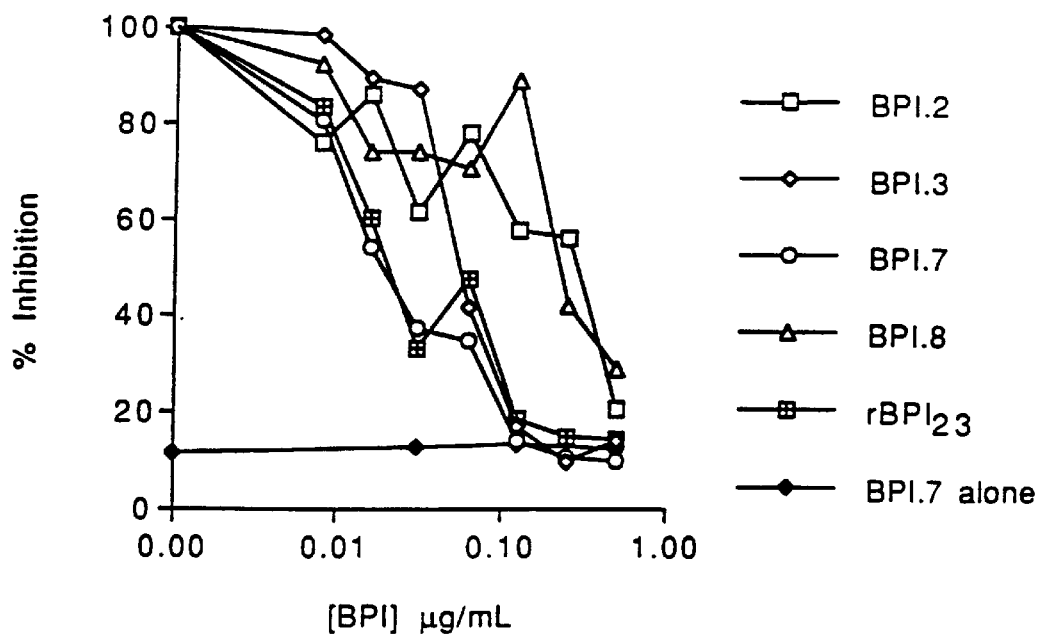
FIGS. 19a and 19b depict graphs showing the effect of synthetic BPI peptides in an LAL inhibition assay.
Figure 19B:
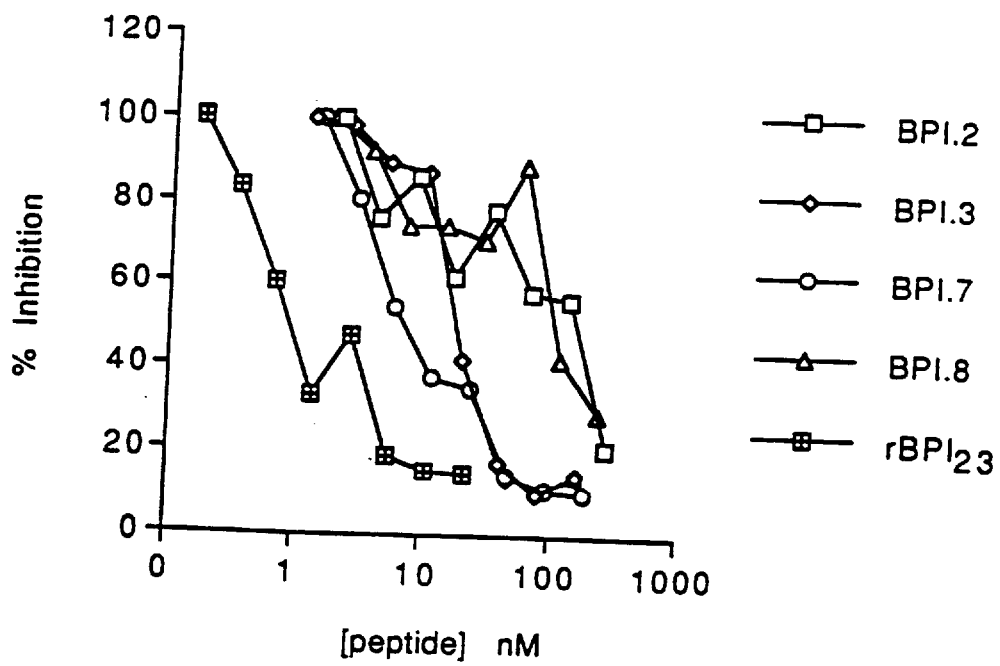

In this example BPI protein product peptides BPI-2, BPI-3, BPI-4, BPI-6, BPI-7, and BPI-8 along with rBPI$_{23}$ were subjected to an LAL assay according to the method of Example 15 to determine their LPS binding and inhibition properties. The results show that BPI-7 and BPI-3 had significant LPS inhibition properties, that BPI-2 and BPI-8 had moderate LPS inhibition properties and that BPI-4 and BPI-6 had no significant LPS inhibition activity as depicted in FIGS. 19a and 19b which depict the sample concentrations as weight or molar concentrations respectively.

EXAMPLE 21

BPI PROTEIN PRODUCT PEPTIDE BACTERICIDAL ASSAY

In this example, BPI protein product peptides BPI-2, BPI-3, BPI-4, BPI-5, BPI-6, BPI-7, BPI-8, BPI-9 and BPI-10 along with $rBPI_{23}$ were tested for bactericidal effects against mutant E. coli J5 (rough) and E. coli 0111:B4 (smooth) bacteria in a radial diffusion assay according to the methods of Example 16. The results depicted in FIGS. 20a–20d show that each of BPI-2, BPI-3, BPI-5, BPI-7, BPI-8, BPI-9 and BPI-10 have greater or lesser degrees of bactericidal activity while BPI-4 and BPI-6 exhibited no bactericidal activity. The bactericidal peptides each tended to be more effective against the rough than the smooth E. coli strain.

Figure 20A:
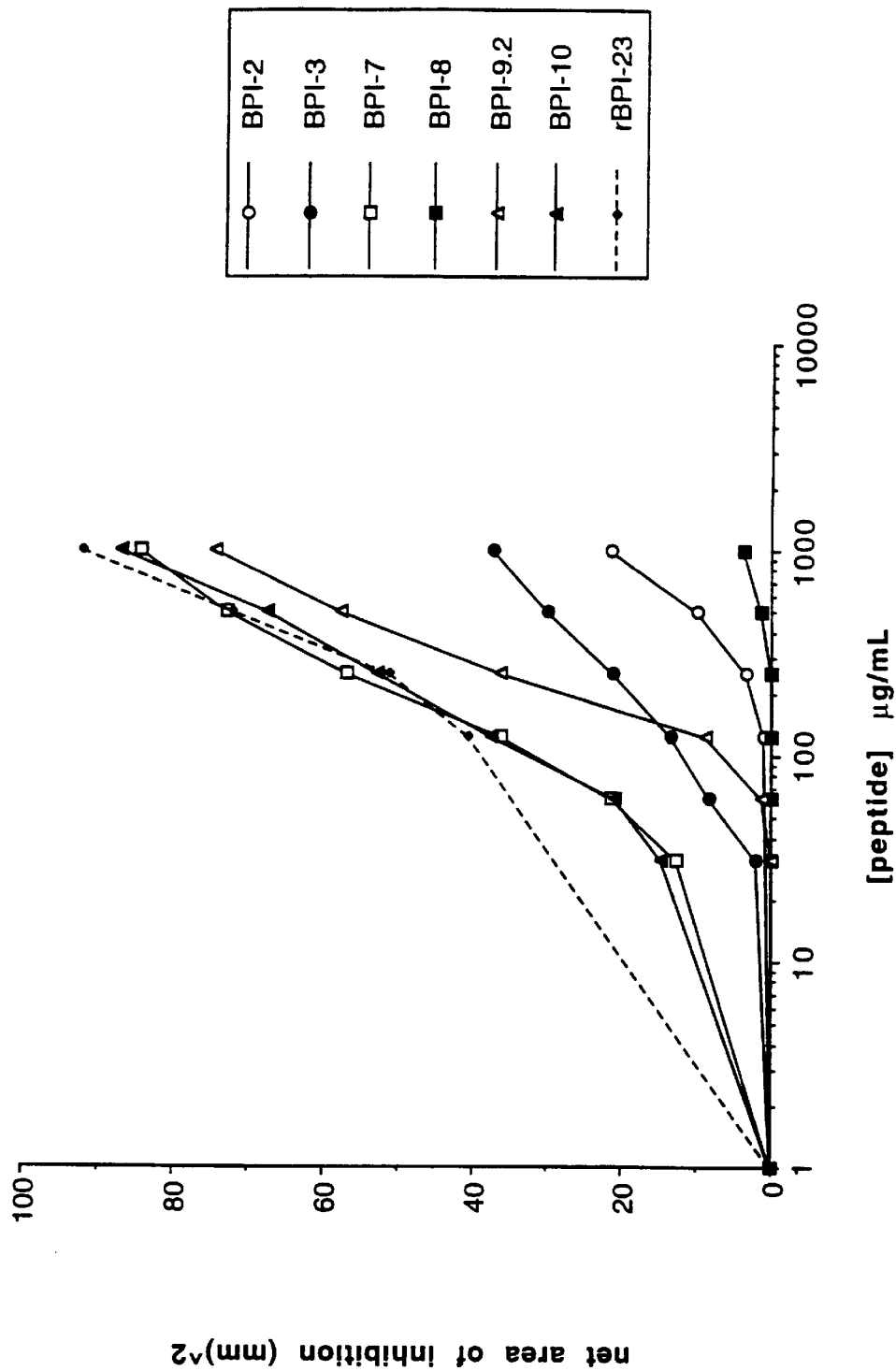
FIGS. 20a, 20b, 20c, and 20d depict graphs showing the effect of synthetic BPI peptides in radial diffusion bactericidal assays.
Figure 20B:
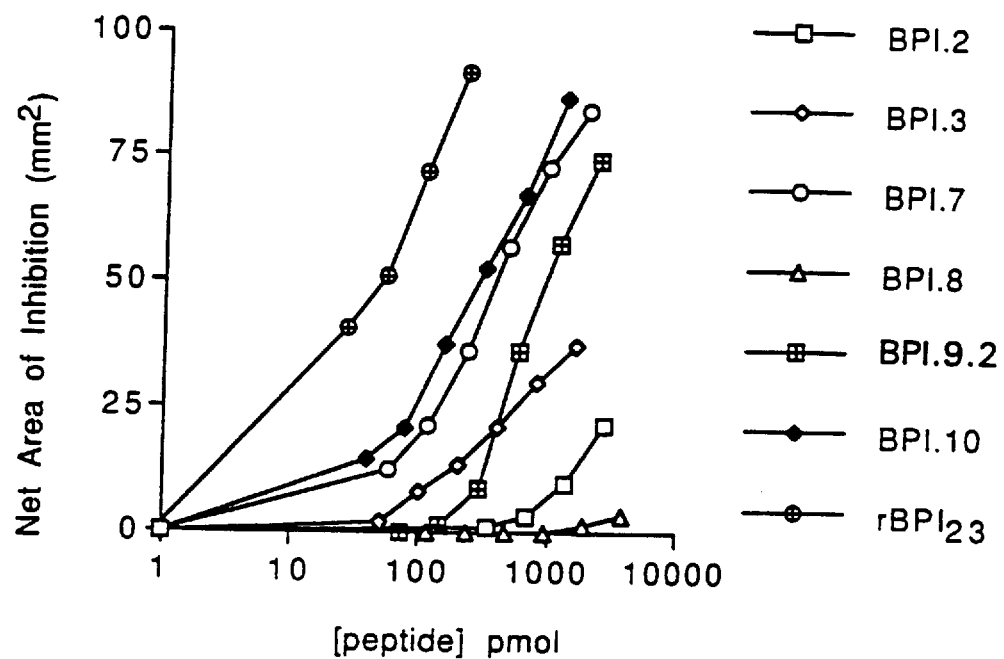
Figure 20C:
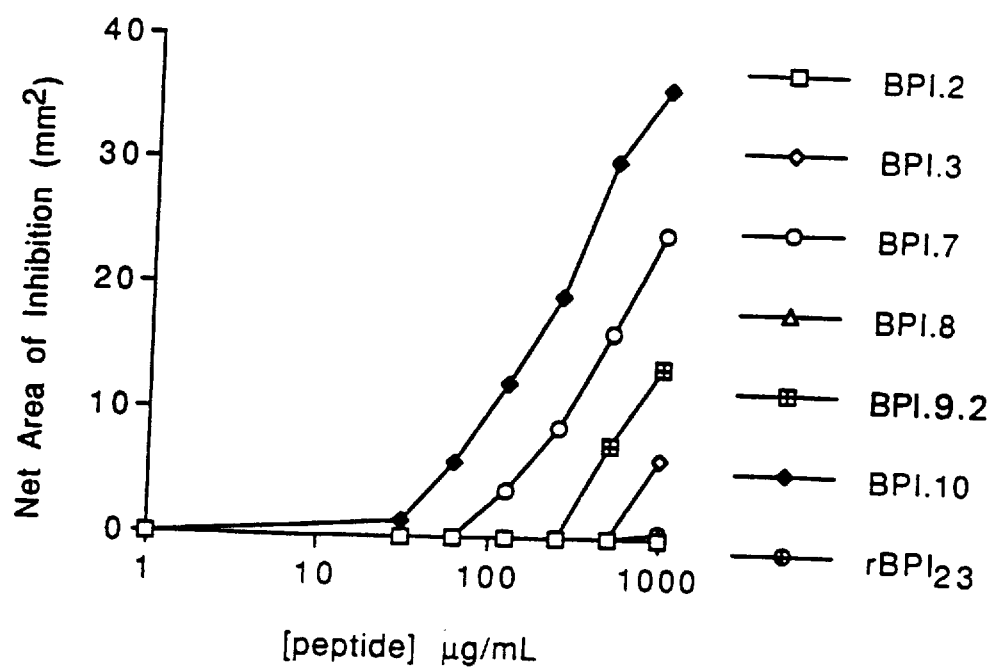
Figure 20D:
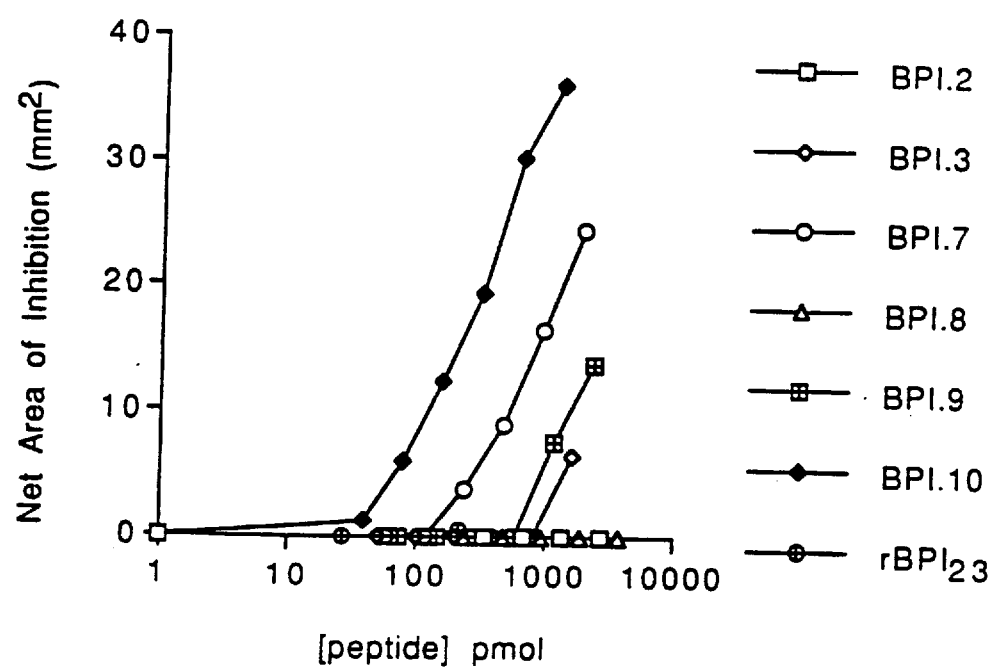
Figure 20E:
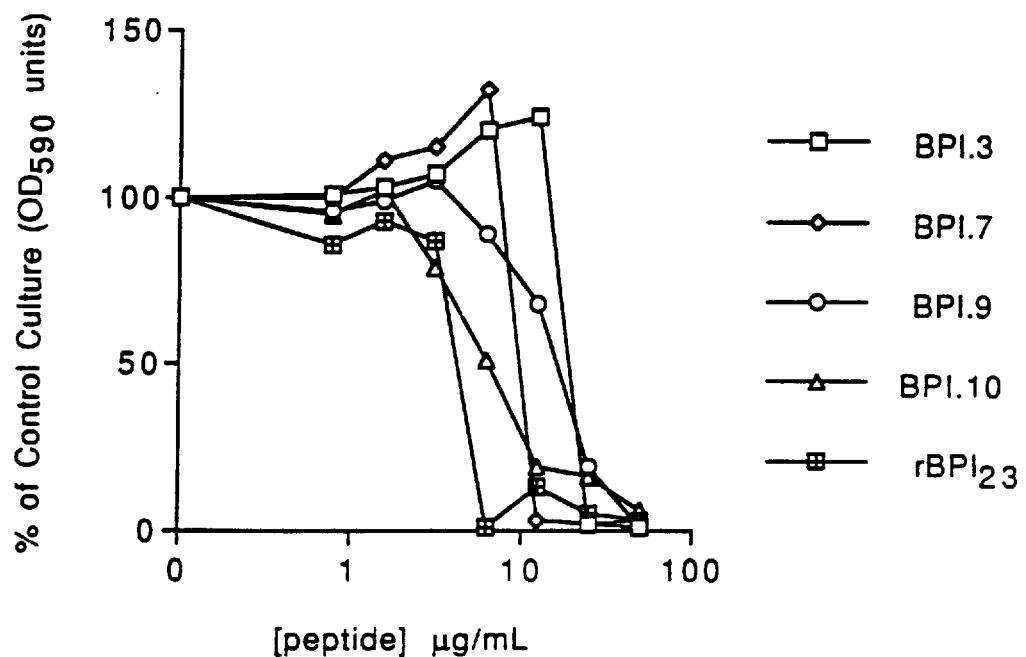
FIGS. 20e and 20f depict graphs showing the effect of synthetic BPI peptides in *E. coli* broth assays.
Figure 20F:
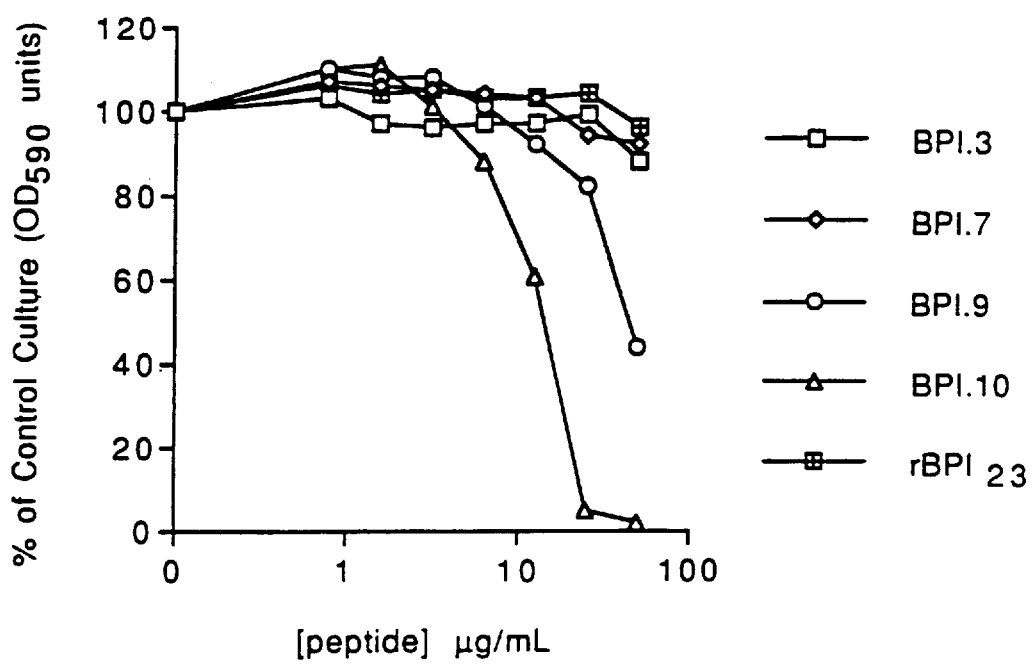

As a further aspect of this example, broth antibacterial assays were conducted to determine the bactericidal activity of certain of the BPI peptides. Specifically either E. coli J5 (rough) and E. coli 0111:B4 (smooth) bacteria were selected from single colonies on agar plates and used to inoculate culture plates to which were added serial ten-fold dilutions of the BPI protein product peptides. The plates were incubated overnight and read on an ELISA plate reader to determine the surviving colony forming units. The results of this assay are depicted in FIGS. 20e (E. coli J5) and 20f (E. coli 0111:B4) which show that BPI protein product peptides BPI-3, BPI-7, BPI-9 and BPI-10 have significant antibacterial activity.

The results of these bactericidal assays along with the heparin binding and LAL assays indicate that there exist small synthetic BPI peptides with one or more of bactericidal, heparin binding and LPS neutralizing effects and that there exist at least three distinct separate functional domains within the 23 kD amino terminal fragment. One domain resides between amino acid residues 17 and 45. A second, the most active domain, characterized by activity in all three assays, resides between amino acids 71 and 99. One specific peptide 86–99 demonstrated activity in all three assays. A third domain is composed of residues 142–169.

EXAMPLE 22

PREPARATION OF BPI PROTEOLYTIC FRAGMENT PEPTIDES

In this example chemical cleavage and enzymatic digestion processes were applied to $rBPI_{23}$, produced according to the procedures of Gazzano-Santoro et al., supra, to develop variously sized proteolytic fragments of the recombinant protein.

The $rBPI_{23}$ was reduced and alkylated prior to proteolysis by cyanogen bromide (CNBr) or endoproteinase Asp-N. The protein was desalted by cold (4° C.) acetone precipitation (1:1 v/v) overnight and pelleted by centrifugation (5000 xg) for 10 minutes. The $rBPI_{23}$ pellet was washed twice with cold acetone and dried under a stream of nitrogen. The $rBPI_{23}$ was then reconstituted to 1 mg/ml in 8M urea/0.1M Tris, pH 8.1 and reduced by addition of 3.4 mM dithiothreitol (Calbiochem, San Diego, Calif.) for 90 minutes at 37° C. Alkylation was performed by the addition of iodoacetamide (Sigma Chemical Co., St. Louis, Mo.) to a final concentration of 5.3 millimolar for 30 minutes in the dark at room temperature. The reduced and alkylated protein was acetone precipitated, centrifuged and washed as described above and the pellet was redissolved for either CNBr or Asp-N digestion.

Prior to CNBr addition, the washed pellet was dissolved in 70% trifluoroacetic acid (TFA) (protein sequencing grade, Sigma) to a final protein concentration of 5 mg/ml. Cyanogen bromide (Baker Analyzed Reagent, VWR Scientific, San Francisco, Calif.) dissolved in 70% TFA was added to give a final 2:1 ratio of CNBr to protein (w/w). This is approximately a 75 fold molar excess of CNBr over methionine residues in the protein. The reaction was purged with nitrogen and allowed to proceed for 24 hours in the dark at room temperature. The reaction was terminated by adding 9 volumes of distilled water, and followed by freezing (–70° C.) and lyophilization.

The reduced and alkylated $rBPI_{23}$ was solubilized at 5.0 mg/ml in 8M urea/0.1 M Tris, pH 8.1. An equal volume of 0.1M Tris, pH 8.1 was added so that the final conditions were 2.5 mg/ml protein in 5M urea/0.1M Tris, pH 8.1. Endoproteinase Asp-N from *Pseudomonas fragi* (Boehringer-Mannheim, Indianapolis, Ind.) was added at a 1:1000 (w/w) enzyme: substrate ratio and the digest was allowed to proceed for 6 hours at 37° C. The reaction was terminated by addition of TFA to a final concentration of 0.1% and the samples were then fractionated by reverse phase HPLC.

The CNBr and Asp-N fragment mixtures were purified on a Zorbax Protein Plus $C_3$ column (4.6×250 mm, 300 Å pore size, MACMOD Analytical Inc, Chadsford, Pa.). A gradient from 5% acetonitrile in 0.1% TFA to 80% acetonitrile in 0.1% TFA was run over 2 hours at 1.0 ml/min. Fragment elution was monitored at 220 nm using a Beckman System Gold HPLC. The column heating compartment was maintained at 35° C. and the fractions were collected manually, frozen at –70° C. and dried in a Speed Vac concentrator. Fragments were then solubilized in 20 mM sodium acetate, pH 4.0/0.5M NaCl prior to use.

Electrospray ionization mass spectrometry was performed on a VG Bio-Q mass spectrometer by Dr. Francis Bitsch and Mr. John Kim in the laboratory of Dr. Cedric Shackleton, Children's Hospital-Oakland Research Institute. Molecular masses were obtained by mathematical transformation of the data.

Figure 21A:
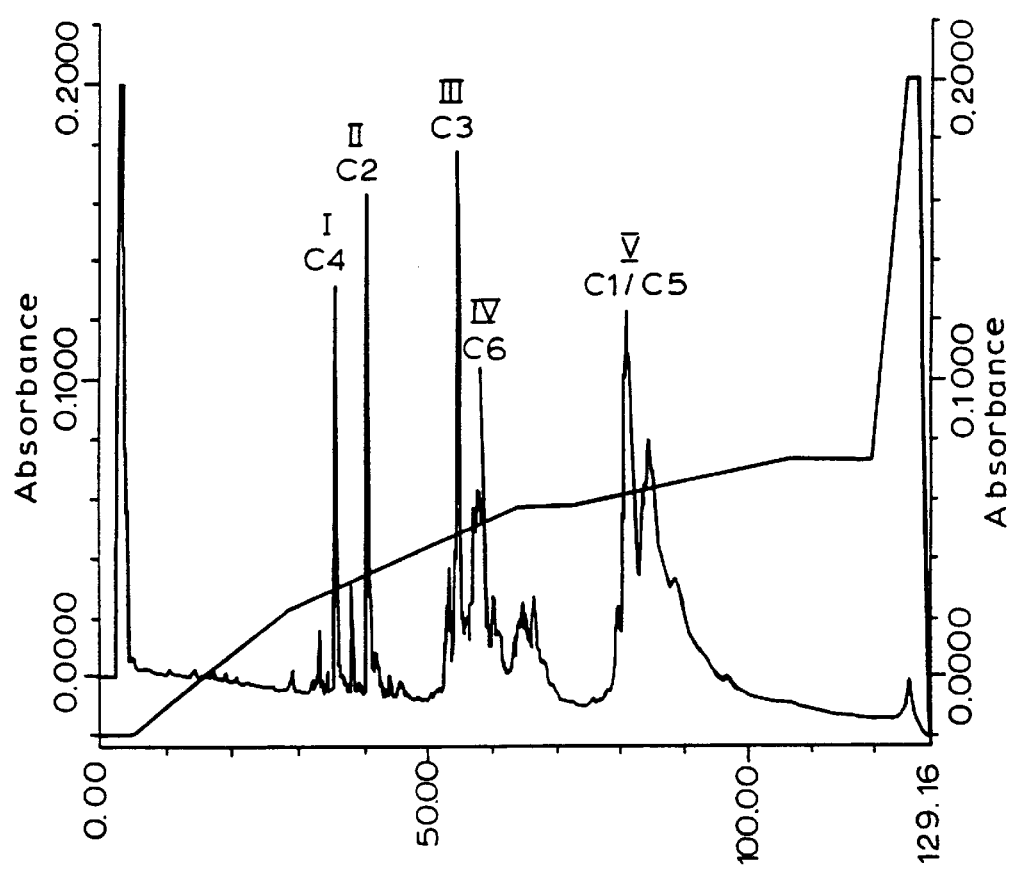
FIGS. 21a and 21b depict HPLC absorbance results for proteolytic fragments of rBPI$_{23}$.

Although the DNA sequence for $rBPI_{23}$ encodes amino acid residues 1–199 of the mature protein, a significant portion of the protein that is produced that is produced is truncated at Leu-193 and Val 195 as determined by electrospray ionization mass spectrometry (ESI-MS). These C-terminal truncations were verified by isolating the C-terminal tryptic peptides, which were sequenced and analyzed by ESI-MS. There are six methionine residues, at positions 56, 70, 100, 111, 170, and 196 and chemical cleavage by cyanogen bromide produced six major peptide fragments as predicted. The results of the CNBr cleavage experiments are summarized in Table 4 (with amino acid numbering according to SEQ ID NO: 2). The fragments were isolated by reverse phase ($C_3$) HPLC (FIG. 21A) and their N-terminal sequences were determined by Edman degradation. The two largest fragments (C1 and C5) were not resolved by the $C_3$ HPLC column and further attempts to resolve them by ion exchange chromatography were unsuccessful, presumably because they are similar in length and isoelectric point. The identities of the C1, C5 fragments within the mixture were determined by ESI-MS. The predicted mass of C1 is 6269 (Table 4), taking into account the loss of 30 a.m.u. resulting from the conversion of the C-terminal methionine to homoserine during the CNBr cleavage reaction. The observed mass of 6251.51±0.34 is consistent with the loss of a water molecule (18 a.m.u.) in a homoserine lactone intermediate, which may be favored over the formation of the homoserine because of the hydrophobicity of the C1 fragment C-terminal amino acids. The predicted mass of the C5 fragment is 6487 and the observed mass is 6385.84±0.39 (Table 1). For the C5 fragment, the C-terminal amino acids are hydrophilic, so the hydrolysis of the homoserine lactone intermediate is probably favored. From both the N-terminal sequencing and the mass spectrum data, the C5 component represents approximately 10–25% of the material in the C1/C5 mixture.

Figure 21B:
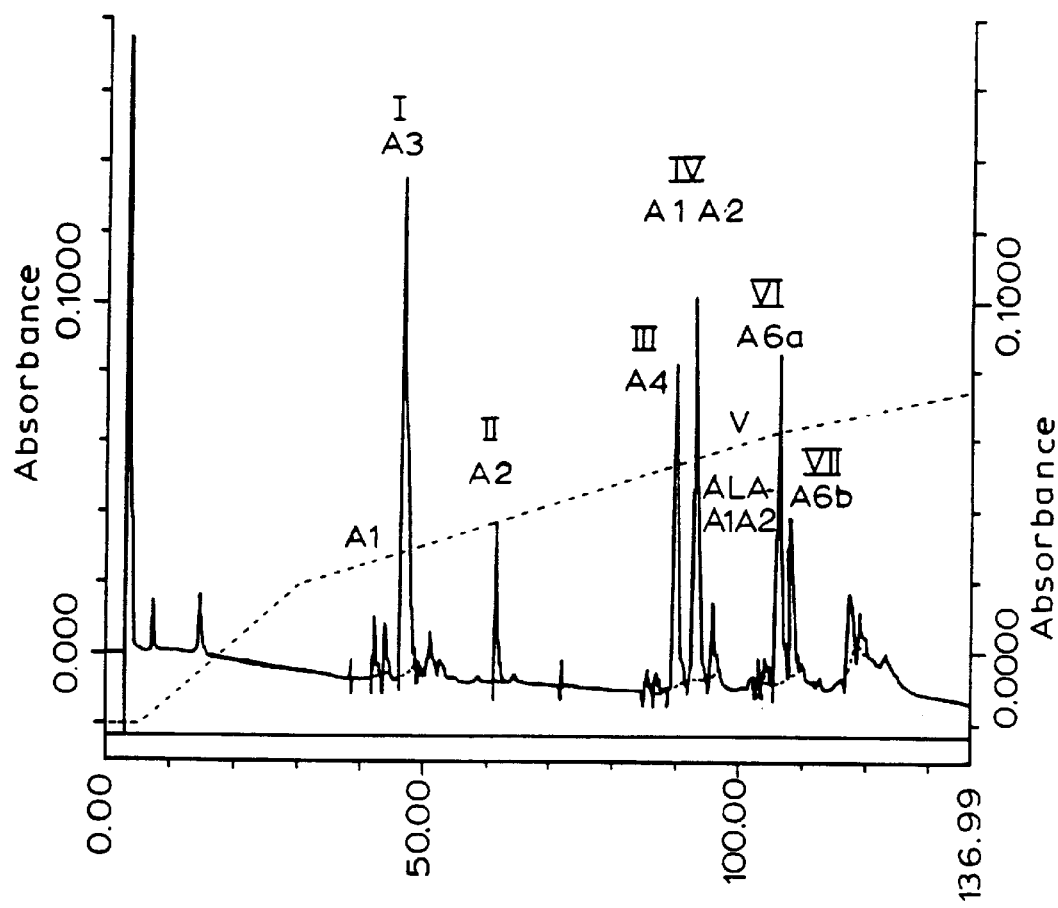

Proteolytic cleavage with endoproteinase Asp-N was performed to provide additional fragments for the regions contained within the CNBr C1/C5 mixture. There are six aspartic acid residues within the $rBPI_{23}$ sequence at positions 15, 36, 39, 57, 105, and 116. The six major Asp-N fragments isolated by $C_3$ HPLC (FIG. 21B) were sequenced and masses were determined by ESI-MS (Table 4). A short duration digest at a 1:1000 (w/w) enzyme:substrate ratio was used to eliminate potential non-specific cleavages, particularly at glutamic acid. It is evident that this digestion did not continue until completion, as one fragment (1–38) was isolated where Asp residues (amino acids 15 and 35) were not cleaved. The mass spectra of the Asp-N fragments were consistent with the predicted masses for each individual fragment. Unlike the CNBr cleavage, where the C-terminal fragment was poorly resolved, the Asp-N fragment from amino acid 116 to the C-terminus was well resolved from all of the other Asp-N fragments.

TABLE 4

SUMMARY OF $rBPI_{23}$ CLEAVAGE FRAGMENT ANALYSIS

| PEAK | SEQUENCE | I.D. | MASS measured | predicted |
|---|---|---|---|---|
| | | CNBr Cleavage Fragments | | |
| I | 101–110 | C4 (101–111) | Not Determined | 1169 |
| II | 57–67 | C2 (57–70) | Not Determined | 1651 |
| III | 71–99 | C3 (71–100) | Not Determined | 3404 |
| IV | 171–194 | C6 (171–196) | Not Determined | 2929 |
| V | 1–25, 112–124 | C1 (1–56), | 6251.51 ± 0.34 | 6299 |
| | | C5 (112–170) | 6485.84 ± 0.39 | 6403 |
| | | Asp-N Proteolytic Fragments | | |
| A | 1–14 | A1 (1–14) | 1465.5 | 1464 |
| I | 39–56 | A3 (39–56) | 2145.2 | 2145 |
| II | 15–38 | A2 (15–38) | 2723.6 | 2724 |
| III | 57–76 | A4 (57–104) | 5442.S | 5442 |
| IV | 1–38 | A1 A2 (1–38) | 4171.4 | 4172 |
| VI | 116–134 | A6a (116–193) | 8800.3 | 8800 |
| VII | 116–128 | A6b (116–195) | 8997.1 | 8996 |

EXAMPLE 23

BACTERICIDAL EFFECTS OF BPI PROTEOLYTIC FRAGMENTS

BPI proteolytic fragments developed according to Example 22 were screened for bactericidal effects rough mutant *E. coli* J5 bacteria in a radial diffusion assay essentially according to the procedures of Example 16. No bactericidal activity was demonstrated for the $rBPI_{23}$ fragments generated by CNBr or by Asp-N digestion, when tested up to 25 pmol/well. This assay detected measurable bactericidal activity with as little as 0.75 pmol of $rBPI_{23}$ per well. Reduced and alkylated $rBPI_{23}$ (up to 100 pmol/well) also was not bactericidal, while alkylated $rBPI_{23}$ retained bactericidal activity equivalent to $rBPI_{23}$.

EXAMPLE 24

HEPARIN BINDING BY BPI PROTEOLYTIC FRAGMENTS $rBPI_{23}$ and BPI proteolytic fragments developed according to Example 22 were employed in heparin binding assays essentially according to the procedures of Example 1.

Heparin binding of CNBr fragments was estimated using 100 picomoles of each fragment per well with a saturating concentration of $^3$H-heparin (20 μg/ml). The results as shown in Table 5 (means of duplicate wells plus or minus the range between the two valves) indicate that the CNBr fragments containing the amino acids 71–100 (C3) and 1–56 and 112–170 (C1,5) bound heparin to a similar extent. The CNBr fragment 171–193 also bound more heparin than the control protein, thaumatin, a protein or similar molecular weight and charge to $rBPI_{23}$.

The Asp-N fragments also demonstrated multiple heparin binding regions in $rBPI_{23}$. As seen in Table 5, the 57–104 Asp-N fragment bound the highest amount of heparin, followed by the 1–38 and 116–193 fragments. These data, in combination with the CNBr fragment data, indicate that there are at least three separate heparin binding regions within $rBPI_{23}$, with the highest capacity residing within residues 71–100.

TABLE 5

Heparin Binding of $rBPI_{23}$ Fragments

| Fragments | Region | cpm $^3$H-Heparin bound |
|---|---|---|
| | CNBr Digest | |
| C1, C5 | 1–56, 112–170 | 82,918 ± 4,462 |
| C2 | 57–70 | 6,262 ± 182 |
| C3 | 71–100 | 81,655 ± 3,163 |
| C4 | 101–111 | 4,686 ± 4 |
| C6 | 171–196 | 26,204 ± 844 |
| | Asp-N Digest | |
| A1 | 1–38 | 17,002 ± 479 |
| A2 | 15–38 | 3,042 ± 162 |
| A3 | 39–56 | 8,664 ± 128 |
| A4 | 57–104 | 33,159 ± 1,095 |
| A6a | 116–193 | 13,419 ± 309 |
| $rBPI_{23}$ | 1–193 | 51,222 ± 1,808 |
| Thaumatin | | 7,432 ± 83 |
| Wash Buffer | | 6,366 ± 46 |

EXAMPLE 25

EFFECT OF BPI PROTEOLYTIC FRAGMENTS ON AN LAL ASSAY

Figure 22:
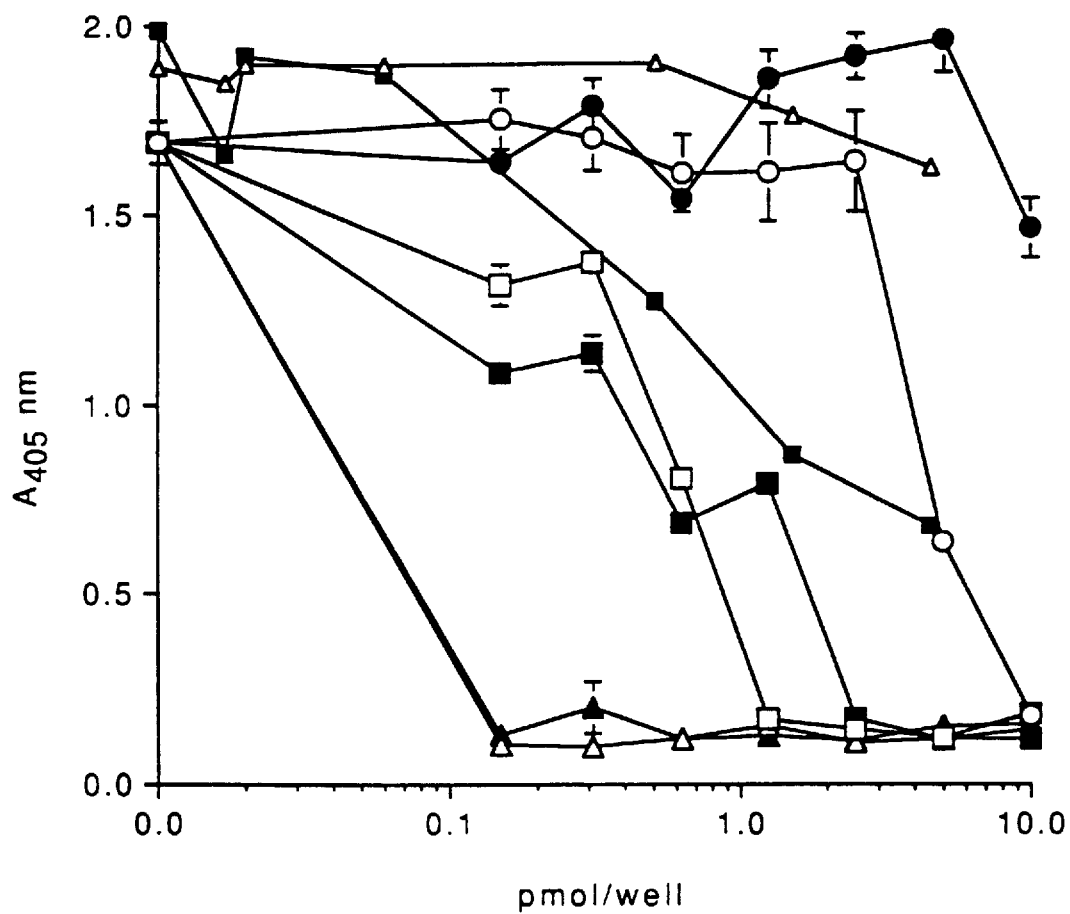
FIG. 22 depicts a graph of LAL inhibition assay results for proteolytic fragments of rBPI$_{23}$.

BPI proteolytic fragments developed according to Example 22 were employed in an LAL inhibition assay essentially as described in Example 15, providing results shown in FIG. 22 wherein: the filled triangle represents $rBPI_{23}$; the open circle represents Asp-N fragment A3; the closed circle represents Asp-N fragment A2; the open square represents Asp-N fragment A3; the filled square represents Asp-N fragment A1A2; the open triangle represents Asp-N fragment A6b; the small open triangle represents CNBr fragment C3; and the small filled square represents CNBr fragment C1/C5.

The CNBr digest fraction containing amino acid fragments 1–56 and 112–170 inhibited the LPS-induced LAL reaction with an $IC_{50}$ of approximately 100 nM. The $IC_{50}$ is approximately 10 fold higher than the $IC_{50}$ for $rBPI_{23}$ (9 nM) in the same assay. The other CNBr digest fragments were non-inhibitory.

A slightly different result was observed with fragments generated from the Asp-N digest, where three fragments were found to be inhibitory in the LAL assay. The fragment corresponding to amino acids 116–193 exhibited LAL inhibitory activity similar to intact $rBPI_{23}$ with complete inhibition of the LPS-induced LAL reaction at 15 nM. The fragments corresponding to amino acids 57–104 and 1–38 also inhibited the LAL assay, but required 10 fold higher amounts. These results, in combination with the CNBr digest results, indicate that at least three regions of the $rBPI_{23}$ molecule have the ability to neutralize LBS activation of the LAL reaction with the most potent region appearing to exist within the 116–193 amino acid fragment.

In related studies of the proteolytic fragments of Example 22 involving ELISA assays using a rabbit polyclonal anti-$rBPI_{23}$ antibody capable of blocking $rBPI_{23}$ bactericidal and LAL inhibition properties and two different, non-blocking mouse anti-$rBPI_{23}$ monoclonal antibodies, the polyclonal antibody was noted to be immunoreactive with the 116–193 and 57–104 Asp-N fragments as well as the 1–56 and 112–170 CNBr fragments while the murine monoclonal antibodies reacted only with an Asp-N fragment representing residues 1–14 of $rBPI_{23}$.

Overall, the results indicate that $rBPI_{23}$ contains three functional domains that contribute to the total biological activity of the molecule. The first domain appears in the sequence of amino acids 17–45 and is destroyed by Asp-N cleavage at residue 36. This domain is moderately active in both the inhibition of LPS-induced LAL activity and heparin binding assays. The second active domain appears in the region of amino acids 65–99 and its inhibition of LPS-induced LAL activity is diminished by CNBr cleavage at residue 70. This domain also exhibits the highest heparin binding capacity and contains the bactericidal peptide, 85–99. The third active domain, between amino acids 142–169, is active in the inhibition of LPS-induced LAL stimulation assay and exhibits the lowest heparin binding capacity of the three regions.

Figure 15:
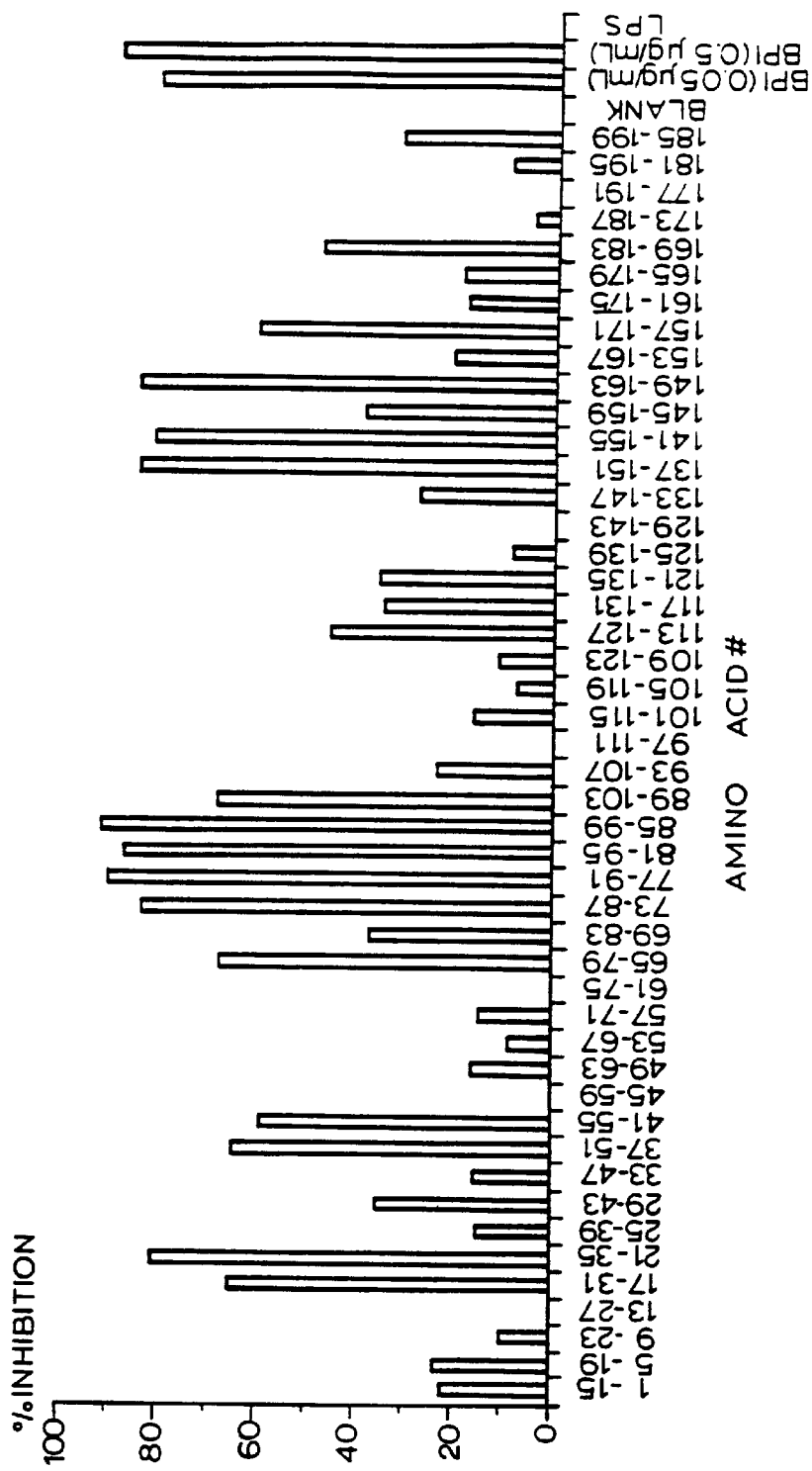
FIG. 15 depicts a graph of a Limulus Amoebocyte Lysate (LAL) inhibition assay for synthetic BPI peptides (with amino numbering according to SEQ ID NO: 2)

Other bactericidal proteins, for example, cecropins and magainins, are characterized by a continuous, amphipathic, α-helical region which is necessary for activity. A high degree of structural similarity was observed between the cationic/hydrophobic motif of LPS binding/bactericidal molecules and the consensus sequences of heparin binding proteins. An excellent correlation exists between the synthetic $rBPI_{23}$ peptides that bind to heparin and those which inhibit the LPS-induced LAL reaction (r=0.75, p=0.0001, n=47) (FIGS. 14 through 16). These data suggest that LPS and heparin may present similar charged arrays to the proteins with which they interact. As a result, other proteins which bind to LPS avidly, may also bind tightly to heparin.

Numerous modifications and variations in the practice of the invention are expected to occur to those skilled in the art upon consideration of the presently preferred embodiments thereof. According to one aspect of the invention, methods of treating gram-negative bacterial infections and the sequelae thereof are contemplated which comprise administration of BPI protein product peptides having gram-negative bactericidal activity. Consequently, the only limitations which should be placed upon the scope of the invention are those which appear in the appended claims.

What is claimed is:

1. A method for inhibiting endothelial cell proliferation comprising administering to a subject an amount of a bactericidal/permeability-increasing protein (BPI) protein product effective to inhibit proliferation of endothelial cells.

2. The method of claim 1 wherein the BPI protein product is an approximately 21 to 25 kD amino-terminal fragment of BPI.

* * * * *